(12) United States Patent  (10) Patent No.: US 7,568,374 B2
Johnson et al.  (45) Date of Patent: *Aug. 4, 2009

(54) GAS FLUX SYSTEM CHAMBER DESIGN AND POSITIONING METHOD

(75) Inventors: Mark A. Johnson, Hickman, NE (US); Andrew G. Ragatz, Lincoln, NE (US); Rex A. Peterson, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/637,201

(22) Filed: Dec. 11, 2006

(65) Prior Publication Data

US 2007/0144276 A1 Jun. 28, 2007

Related U.S. Application Data

(63) Continuation-in-part of application No. 11/217,922, filed on Sep. 1, 2005, now Pat. No. 7,509,836.

(51) Int. Cl.
    *G01N 33/24* (2006.01)
(52) U.S. Cl. .................... 73/19.01; 73/863.21
(58) Field of Classification Search ........... None
    See application file for complete search history.

(56) References Cited

U.S. PATENT DOCUMENTS

| 4,444,041 | A | * | 4/1984 | Zison | ................. | 73/19.04 |
| 5,355,739 | A | * | 10/1994 | Cooper et al. | ............. | 73/864.73 |
| 5,394,949 | A | * | 3/1995 | Wright et al. | ................. | 175/20 |
| 6,598,458 | B1 | | 7/2003 | Edwards et al. | | |
| 6,692,970 | B2 | | 2/2004 | Butnor et al. | | |
| 6,843,082 | B2 | | 1/2005 | Vickers | | |
| 2002/0000226 | A1 | | 1/2002 | Butnor et al. | | |
| 2002/0100860 | A1 | | 8/2002 | Wieder | | |
| 2006/0117840 | A1 | * | 6/2006 | Furtaw et al. | ................. | 73/149 |
| 2007/0044538 | A1 | * | 3/2007 | Johnson et al. | ............ | 73/19.01 |

FOREIGN PATENT DOCUMENTS

JP 0733129 A * 12/1995

OTHER PUBLICATIONS

U.S. Appl. No. 11/063,955, "Pressure Vent, Leak Detection, and Kinetic Volume Determination Methods and Systems," inventors: Michael D. Furtaw, Dayle K. McDermitt, and Liukang Xu; filed Feb. 22, 2005.

(Continued)

*Primary Examiner*—Hezron Williams
*Assistant Examiner*—Rose M Miller
(74) *Attorney, Agent, or Firm*—Townsend and Townsend and Crew LLP

(57) ABSTRACT

A gas flux chamber assembly is provided that includes a lift-and-rotate mechanism and a chamber. The chamber is moved between first and second positions, wherein the chamber is positioned over a sample in the first position and is positioned outside of an area above the sample in the second position. In operation, the chamber is first lifted off of the collar and is then rotated, about a rotational axis outside of the area above the collar. These acts are reversed to move the chamber from the second position to the first position.

48 Claims, 13 Drawing Sheets

OTHER PUBLICATIONS

United States Patent and Trademark Office Action dated Dec. 28, 2007 for Case No. U.S. Appl. No. 11/217,922, filed Sep. 1, 2006.

G.L. Hutchinson and G.P. Livingston, "Vents and seals in non-steady-state chambers used for measuring gas exchange between soil and the atmosphere", European Journal of Soil Science, vol. 52, pp. 675-682 (2001).

J.M. Welles, T.H. Demetriades-Shah and D.K. McDermitt, "Considerations for measuring ground CO2 effluxes with chambers," Chemical Geology, vol. 177, pp. 3-13 (2000).

F. Conen and K.A. Smith, "A re-examination of closed flux chamber methods for the measurement of trace gas emissions from soils to the atmosphere," European Journal of Soil Science, vol. 49, pp. 701-707 (1998).

N.T. Edwards, "A moving chamber design for measuring soil respiration rates," Oikos, vol. 25, pp. 97-101 (1974).

B.A. Kimball, "Canopy gas exchange: Gas exchange with soil," Limitations to efficient water use in crop production published by ASA-CSSA-SSSA, pp. 215-226 (1983).

"SRS-1000 Portable Soil Respiration System," ADC BioScientific Ltd., 2 pages (Oct. 2003).

"S.O.A.P. Static Outside Air Probe," Air Monitor Corporation, 2 pages (May 2000).

"Static Pressure Reference Probe for Outdoor Use," Micatrone, 2 pages (2002).

"SPH10/20 Static Pressure Heads for Minimizing Wind Induced Error," Vaisala, 2 pages (2003-2004).

"Meteorological Measurement Systems," Paroscientific, Inc., 2 pages (2001).

"Design and Characteristics of the MET3A High-Performance Dual Pressure Port," Paroscientific, Inc., 5 pages (2000).

"MET3A Meteorological Measurement System," Paroscientific, Inc., 2 pages (1999).

"Model 61002 Gill Pressure Port," R.M. Young Company, 1 page (2000).

"Model 61202 Barometric Pressure Sensor," R.M. Young Company, 1 page (2004).

"The 6400-09: Soil CO2 Flux Chamber," LI-COR Biosciences, 2 pages (1997).

"LI-8100 Automated Soil CO2 Flux System," LI-COR Biosciences, 8 pages (Dec. 8, 2003).

Photograph of the LI-8100 Survey Chamber, 1 page, shown Oct. and Nov. 2003.

Photograph of the LI-8100 Long-Term Chamber, 1 page, shown Dec. 8, 2003.

"The Impact of Pressure Perturbation on Chamber-Based Soil CO2 Efflux Measurement," Xu et al., 1 page, presented at American Geophysical Union meeting Dec. 7, 2004.

Automated Monitoring of Soil Respiration: A Moving Chamber Design, Nelson T. Edwards* and Jeffery S. Riggs, p. 1266-1271, (2003).

Dynamax, Soil Respiration Chamber SRC-MV5, 1 page, (2003).

PP Systems Data Sheet, SRC-1 Soil $CO_2$ Flux System, "A closed system for accurate measurement of soil $CO_2$ flux;" Feb. 18, 2005, 2 pages.

PP Systems Data Sheet, CFX-2 Soil $CO_2$ Flux System, "An open system for accurate measurement of soil $CO_2$ flux;" Apr. 4, 2005, 2 pages.

Westsystems, Continuous Monitoring Station, http://www.westsystems.com/cm_fixed_station.html; Aug. 15, 2005, 3 pages.

West Systems Portable soil flux meter, http://www.westsystems.com/documentation/SoilFluxPortableBrouchure0503.pdf; 2 pages, Dec. 2007.

Soil CO2 Flux System, Soil CO2 Chamber snapshots, http://www.insituflux.org/CO2Chambersnapshots.html; Printed Aug. 15, 2005, 2 pages.

Soil CO2 Flux System, System snapshots, http://www.insituflux.org/systemksnapshots.html; Printed Aug. 15, 2005, 1 page.

Automated Carbon Efflux System Patented, SRS Researchers Patent Automated Carbon Efflux System, http://www.srs.fs.usda.gov/about/newsrelease/nr_2004-02-25-butnor.htm; Feb. 25, 2004, 2 pages.

Automatic Carbon Efflux System, A.C.E.S.—USDA Forest Service SRS-4154, The Automatic Carbon Efflux System (A.C.E.S), http://www.srs.fs.usda.gove/soils/research/aces.html; Jul. 7, 2003, 4 pages.

* cited by examiner

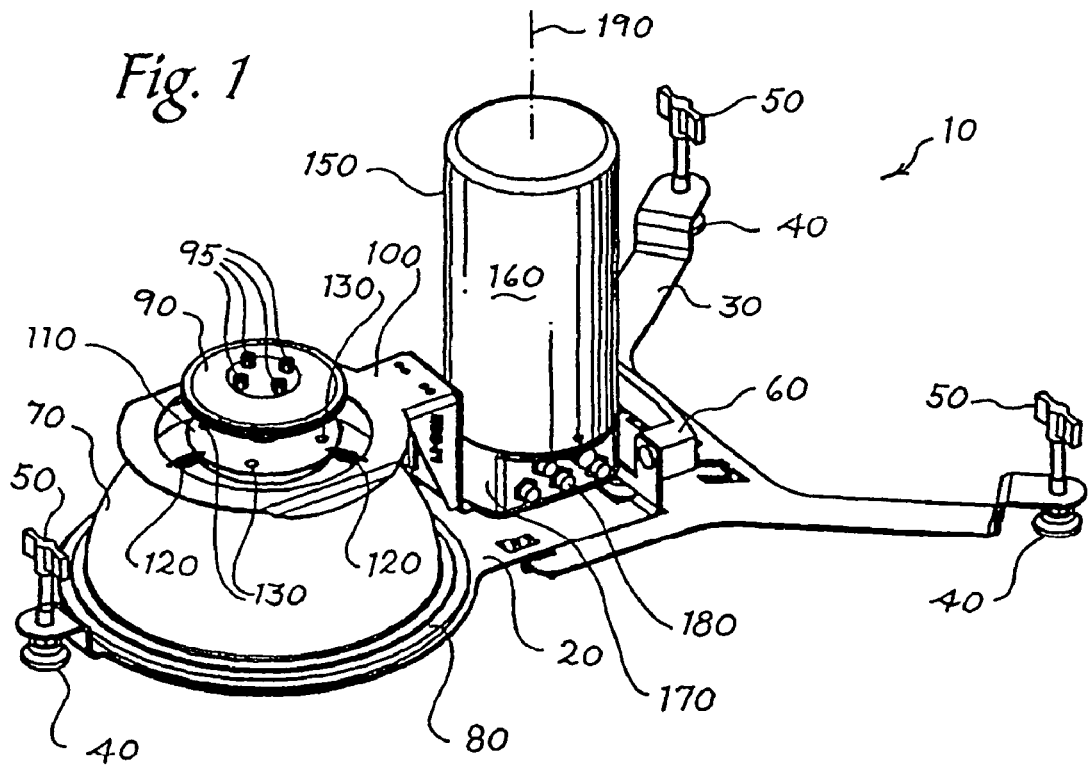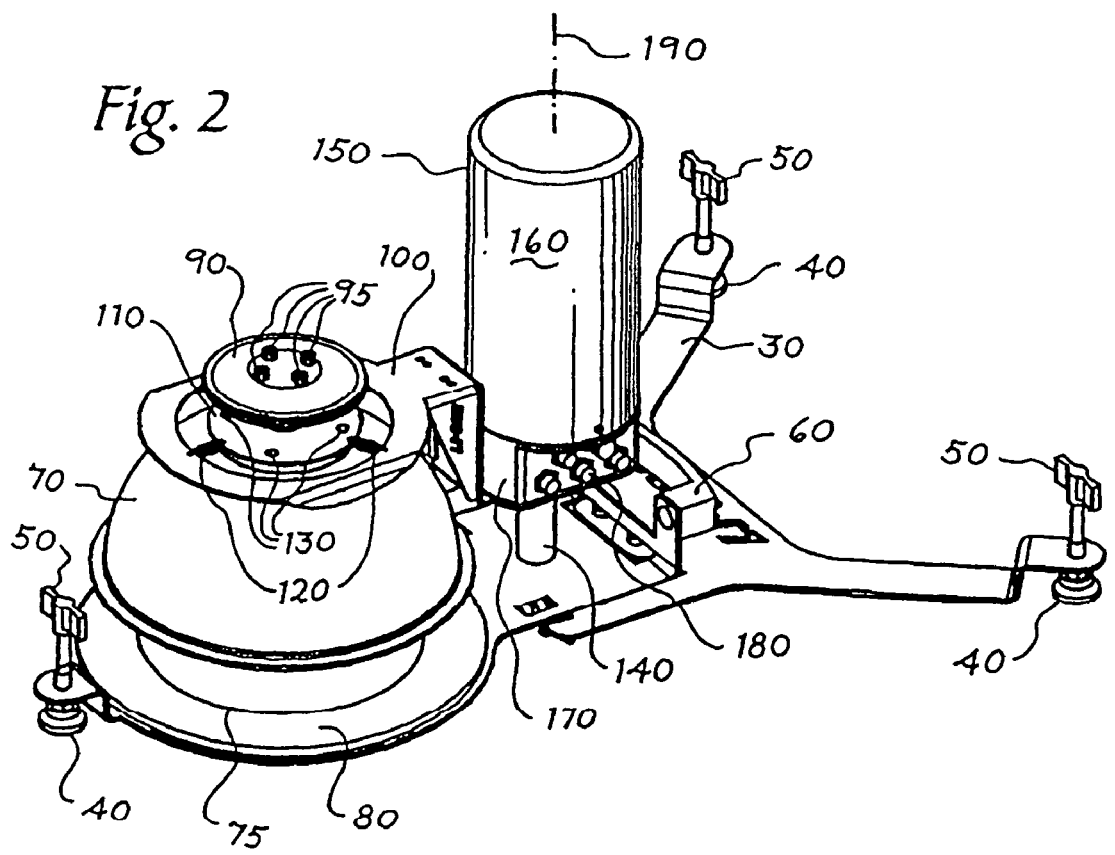

GAS FLUX SYSTEM CHAMBER DESIGN AND POSITIONING METHOD

CROSS REFERENCE TO RELATED APPLICATION

This application is a continuation-in-part of application Ser. No. 11/217,922, which is expressly incorporated by reference.

BACKGROUND

Gas flux chamber assemblies are used to measure trace gas emissions (e.g., $CO_2$ and methane) from soils. One such assembly is the LI-8100 Long-Term Chamber by LI-COR Biosciences. The LI-8100 Long-Term Chamber is electrically actuated via a geared, motorized chain drive mechanism to move a chamber between two positions—one over the soil sampling area and another away from the soil sampling area. Trace gas emissions are measured when the chamber is over the soil sampling area. When measurements are not being taken, the chamber is moved away from the sampling area to expose the soil to the environment, thereby allowing environmental factors (e.g., wind, rain, sun, etc.) to reach the soil just as it would if the chamber were not present. This allows a researcher to measure soil $CO_2$ flux in as representative an environment as possible, thereby ensuring maximum yield from the sample area.

The LI-8100 Long-Term Chamber uses a strut mechanism to move the chamber through a seven-inch radius vertical circular arc over and away from the sampling area. The strut mechanism maintains the chamber opening downward to avoid collection of precipitation and debris while in the open or moving state. The unique advantage of the LI-8100 Long-Term Chamber as compared to other chamber designs is the ability to move the chamber clear from the sampling area, which is important for long-term unattended measurements. An unobstructed sampling area allows natural exposure to sunlight, shading, precipitation, and temperature effects, thereby minimizing the influence of the testing equipment on the measured gas flux. In contrast, assemblies that simply move a chamber directly above the sampling area can shade the sampling area with the chamber, thereby creating an artificial condition that can influence the flux measurements. Also, in systems where the chamber is stationary and a movable chamber lid covers and uncovers the chamber, the chamber itself protrudes from the soil surface even when a measurement is not being taken and obstructs the sampling area.

SUMMARY

The present invention is defined by the following claims, and nothing in this section should be taken as a limitation on those claims.

By way of introduction, in one preferred embodiment, a gas flux chamber assembly is provided comprising a lift-and-rotate mechanism and a chamber. The chamber is moved between first and second positions, wherein the chamber is positioned over a soil sample in the first position and is positioned outside of an area above the soil sample in the second position. In operation, the chamber is first lifted off of the soil collar and is then rotated, about a rotational axis, outside of the area above the soil sample. These acts are reversed to move the chamber from the second position to the first position. Other preferred embodiments are provided, and each of the preferred embodiments described herein can be used alone or in combination with one another.

The preferred embodiments will now be described with reference to the attached drawings.

BRIEF DESCRIPTION OF THE DRAWINGS

FIG. 1 is an illustration of a gas flux chamber assembly of a preferred embodiment in which a chamber is in a first, closed/sampling position.

FIG. 2 is an illustration of a gas flux chamber assembly of a preferred embodiment in which a chamber is in a raised, lift position.

DETAILED DESCRIPTION OF THE PRESENTLY PREFERRED EMBODIMENTS

Figure 3:
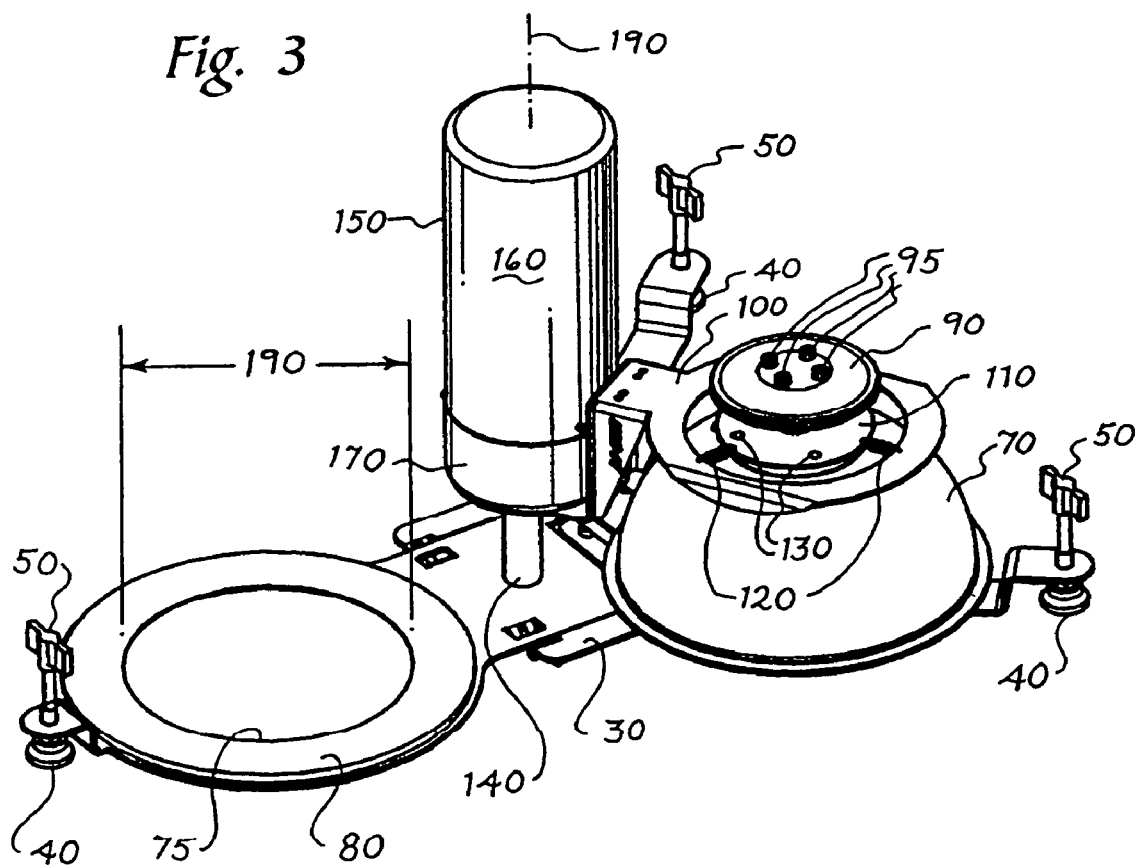
FIG. 3 is an illustration of a gas flux chamber assembly of a preferred embodiment in which a chamber is in a second, fully open/rotate position.

By way of introduction, the preferred embodiments presented herein describe a gas flux chamber with a lift-and-rotate method to move a sampling chamber to and from a monitoring area. The rigid sampling volume provides for true constant-volume measurements. When sampling is completed, the method first lifts the sampling chamber off of a soil collar and then rotates the chamber completely free of the sampling area. This exposes the sampling area to natural wind, precipitation, temperature, and sunlight. The exposure of the sampling area provides minimal disturbance of the soil microclimate, allowing long-term unattended measurements. When a measurement is commanded, the chamber is again rotated directly above the sampling area and gently lowered onto the sampling collar. While this lift-and-rotate can be performed with any suitable lift-and-rotate mechanism, one of the preferred embodiments presented herein describes a mechanism that produces the lift-and-rotate motion with a minimum of moving parts. Further, the entire operating mechanism in this preferred embodiment is enclosed in a sealed cylindrical column that requires no periodic maintenance. The simplicity of this preferred lift-and-rotate mechanism allows a smaller mechanism footprint, reduces complexity, and reduces cost. Further, these preferred embodiments replicate the advantages of the LI-COR LI-8100 Long-Term Chamber through a much simpler and more compact motion.

Turning now to the drawings, FIG. 1 is an illustration of a chamber assembly 10 of a preferred embodiment. The assembly 10 comprises a base 20 coupled with support legs 30. As used herein, the phrase "coupled with" means directly coupled with or indirectly coupled with through one or more components (named or unnamed herein). The support legs 30 comprise a plurality of feet 40 and thumbscrews 50 for adjusting the height of the feet 40 so the feet 40 rest on the ground. These components help ensure a stable, non-moving position when the assembly 10 is installed in a sample area. The adjustable support legs also introduce a three-point leveling mechanism for the chamber assembly 10 such that the chamber assembly 10 can be leveled with respect to the soil collar 75. The base 20 comprises a handle 60, which allows the chamber assembly 10 to be hand-carried and deployed in any desired location.

The assembly 10 also comprises a chamber 70. In FIG. 1, the chamber 70 is shown in a first position on a soil collar 75 that is embedded in soil to be observed (the soil collar is not shown in FIG. 1 but is shown in FIGS. 2 and 3). The soil collar 75 preferably has a minimal protrusion above the soil surface to minimize the impedance to sunlight, wind, precipitation and other exposure to the sampling area. A collar seal 80 coupled with base 20 is a gasket that helps form a gas-tight seal between the chamber 70 and the soil collar 75 and causes flux of trace gas emissions from the soil to move in a vertical direction. Preferably, the height of protrusion of the soil collar 75 above the soil surface is the thickness of the collar seal 80, which in a presently preferred embodiment, is less than 0.5 inches.

The assembly also comprises a vent 90 coupled with the chamber 70. The vent has four thumbscrews 95 for disassembling the vent 90 for cleaning. The vent 90 maintains the ambient soil surface pressure within the chamber 70 by compensating for the effect of wind on the air pressure at the soil surface. U.S. patent application Ser. No. 11/063,955, which is assigned to the assignee of the present invention and is hereby incorporated by reference, describes a presently preferred vent.

The chamber 70 is coupled with a support structure 100 via a spring disk 110 and three extension springs 120 oriented horizontally. The spring disk 110 is attached to the chamber 70 with screws 130 in this preferred embodiment, and the springs 120 support the chamber 70 radially around the circumference of the ring on one end of the support structure 100. Accordingly, the chamber support structure 100 is compliantly coupled to the chamber 70 through the three extension springs 120. An analogous design can be seen in consumer trampolines, in which an inextensible fabric is horizontally supported by extension springs around its periphery. The extension springs 120 allow the chamber 70 to "float" so that exact parallelism between the chamber support structure 100 and the collar seal 80 is not required. Moreover, through appropriate choice of spring rates, the downward force on the chamber 70 can be made a weak function of the position of the chamber support structure 100. This allows the chamber support structure 100 to be coarsely positioned by the lift-and-rotate mechanism without having a significant impact on the magnitude of the sealing force between the chamber 70 and the collar seal 80. This avoids the cost and complexity of designing a constant-force mechanism to maintain a constant sealing force between the chamber 70 and collar seal 80. A simpler and cheaper kinematic positioning mechanism is implemented along with a compliant structure that applies nearly the same force regardless of kinematic imperfections (e.g., dimensional tolerances, relaxation of gasketing mateterials, variations in assembled dimensions, etc.) In a presently preferred embodiment, the extension springs 120 have a spring constant of 19 lbs/inch and are stainless steel. A suitable spring is part number 80404S from Century Spring.

The other end of the support structure 100 is coupled with an outer column 310. The outer column 310 is not shown in FIG. 1, as it is contained in the enclosure 150 when the chamber 70 is in the first position, but will be described below with respect to FIGS. 2 and 3. In this preferred embodiment, the enclosure 150 contains a lift-and-rotate mechanism, which will be described below. The outer column 310 forms one component of the lift-and-rotate mechanism of this preferred embodiment. The enclosure 150 contains a top half 160 shaped like an inverted can and a bottom half 170 with electrical connectors 180 for controlling the movement of the chamber 70 and for connecting soil temperature probe(s), soil moisture probe(s), and a power supply. In a presently preferred embodiment, the top half of the enclosure 160 is a deep-drawn aluminum can that is powder coated to make it robust to weather and mechanical abuse, and the bottom half 170 is cast aluminum and powder coated.

In this preferred embodiment, the lift-and-rotate mechanism moves the chamber 70 between a first position, in which the chamber 70 is positioned on the soil collar, to a second position, in which the chamber 70 is positioned outside of an area above the soil collar. This movement is shown in FIGS. 1-3. In FIG. 1, the chamber 70 is in the first position, which will also be referred to herein as the closed or sampling position. The soil sampling area is directly beneath the hemispherical chamber 70. It is in this first position that a gas analyzer (not shown) coupled with the chamber 70 with gas inlet and outlet conduits (not shown) measures the change in concentration over time of a gas leaving or entering the soil, which indicates the flux rate of the gas moving from/to the soil to/from the atmosphere. When the measurement is complete, the lift-and-rotate mechanism moves the chamber 70 from the first position to the second position by lifting the chamber 70 vertically off of the soil collar 75 (shown in FIG. 2).

As shown in FIG. 2, the radius of the soil collar 75 is smaller than the radius of the chamber 70 in this embodiment, and the collar seal 80 seals the connection between the chamber 70 and the soil collar 75. Accordingly, in this embodiment, the chamber 70 is "on" the soil collar 75 when the chamber 70 is on the collar seal 80. In other embodiments where the radius of the soil collar 75 more closely matches the radius of the chamber 70, the chamber 70 is "on" the soil collar 75 when the chamber 70 directly contacts the soil collar 75. Accordingly, the phrase "on the soil collar" as used in the claims should be interpreted to cover implementations where the chamber is directly on the soil collar or indirectly on the soil collar though the use of a collar seal or some other intermediary component.

Preferably, the chamber 70 is lifted only as high as necessary to clear the protrusion of the soil collar 75. Once the chamber 70 has been lifted sufficiently clear of the soil collar 75, the lift-and-rotate mechanism rotates the chamber 70 about a vertical rotational axis 190 of the lift-and-rotate mechanism outside of the area 190 above the soil collar 75, completely clear of the sampling area (see FIG. 3). The vertical rotational axis 190 is substantially parallel to the soil collar 75 (depending on ground conditions and the installation of the soil collar 75, the soil collar 75 may not be exactly parallel to the vertical rotational axis 190). The orientation of the chamber 70 is maintained in a downward facing direction to avoid the accumulation of precipitation and/or debris. In addition to avoiding the accumulation of precipitation and/or debris, the downward orientation avoids the creation of a bluff body. During windy conditions, the soil chamber can act as a sail on the assembly and cause the entire assembly to vibrate, shift, and potentially tip. Maintaining the chamber in a downward orientation keeps the assembly 10 more stable in windy conditions. In contrast, a clamshell design, in which the chamber or chamber lid is rotated about an axis substantially perpendicular to the soil collar axis, can create a significant bluff body, causing assemblies analogous to assembly 10 to become unstable in windy conditions. When a measurement is initiated, the reverse order of steps just described is performed, with the chamber 70 being rotated directly above the sampling area and then gently lowered onto the soil collar 75.

The lift-and-rotate mechanism minimizes the footprint of the mechanical mechanism used for chamber 70 movement. The simplicity of the core mechanism allows for a minimal number of moving parts, thus significantly reducing both the material and manufacturing costs. The entire mechanism is enclosed in the weather-tight enclosure 150, preferably using static sealing design. The enclosure 150 preferably has only a single dynamic penetration, which is sealed against the elements using a rod-wiper/seal combination popular in hydraulic-cylinder actuator applications.

At the core of the lift-and-rotate mechanism in this preferred embodiment is a simple mechanism that converts the rotary motion of an electric motor to first a translational, and then rotational motion. The operating principle behind the lift-and-rotate mechanism is illustrated schematically in FIGS. 4A-4D, which illustrate the operating principle using a linear motion analogy. Once the linear motion analogy is understood, the translation to rotary motion is straightforward. Consider two slots 200, 210 cut into two different plates. Suppose that these plates are constrained to each other so that they may slide relative to each other right and left, but they may not slide up and down. Further, assume that a pin 220 passes through both slots 200, 210. Geometrically, the pin 220 can be thought of as the intersection point of the two slots 200, 210. For illustration, assume slot 210 is fixed, and slot 200 can translate left-to-right with respect to slot 210. Starting with FIG. 4A, assume that slot 200 begins to move toward the right. The motion of slot 200 moves the intersection point of the two slots 200, 210, and the pin 220 subsequently follows. The pin 220 will move to the right in slot 210 until it can no longer do so (see FIG. 4B). When the pin 220 enters the vertical portion of slot 210, it can no longer move to the right. Meanwhile, slot 200 continues to translate to the right, and the intersection point of the two slots 200, 210 continues upward. The pin 220, constrained in both slots 200, 210, subsequently moves upward also (see FIG. 4C). Finally, as slot 200 continues to move to the right, the pin 220 reaches the top of slot 210 (see FIG. 4D). The pin 220 can be lowered and returned to its starting position by reversing the steps just described. The unique intersection point of the two slots 200, 210 creates a reversible mechanism with a single-valued state. The single-valued state of the mechanism simplifies the control of the mechanism since the location of the pin 220 within the L-shaped slot 210 completely defines the state of all moving components of the mechanism.

Figure 4A:
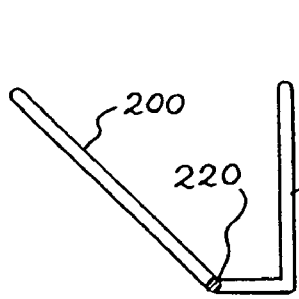
FIGS. 4A-4D are illustrations of conceptual linear slot geometry analogous to that used to create lift and rotate motion of a preferred embodiment.
Figure 4B:
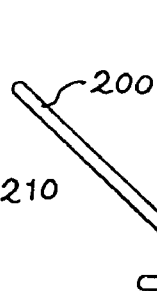
Figure 4C:
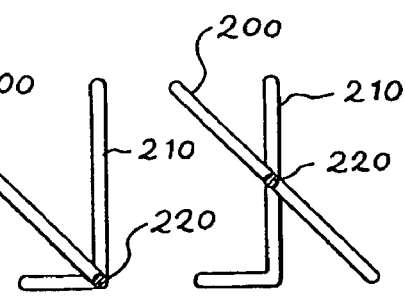
Figure 4D:
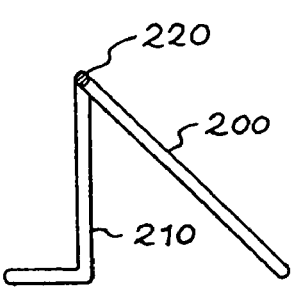

If one considers only the motion of the pin 220 from left to right in FIG. 4A, it first translates horizontally within slot 200, moving at exactly the same speed as slot 200. When the pin 220 encounters the turn in slot 210, it begins to rise vertically within slot 210. Note that the pin's 220 speed during the vertical rise is no longer the same speed as slot 200 but is rather a function of the speed of slot 200 along with the slope of slot 200. Sloping slot 200 further toward the horizontal produces slower rise speeds while slopes nearer the vertical produce faster rise speeds.

Figure 5:
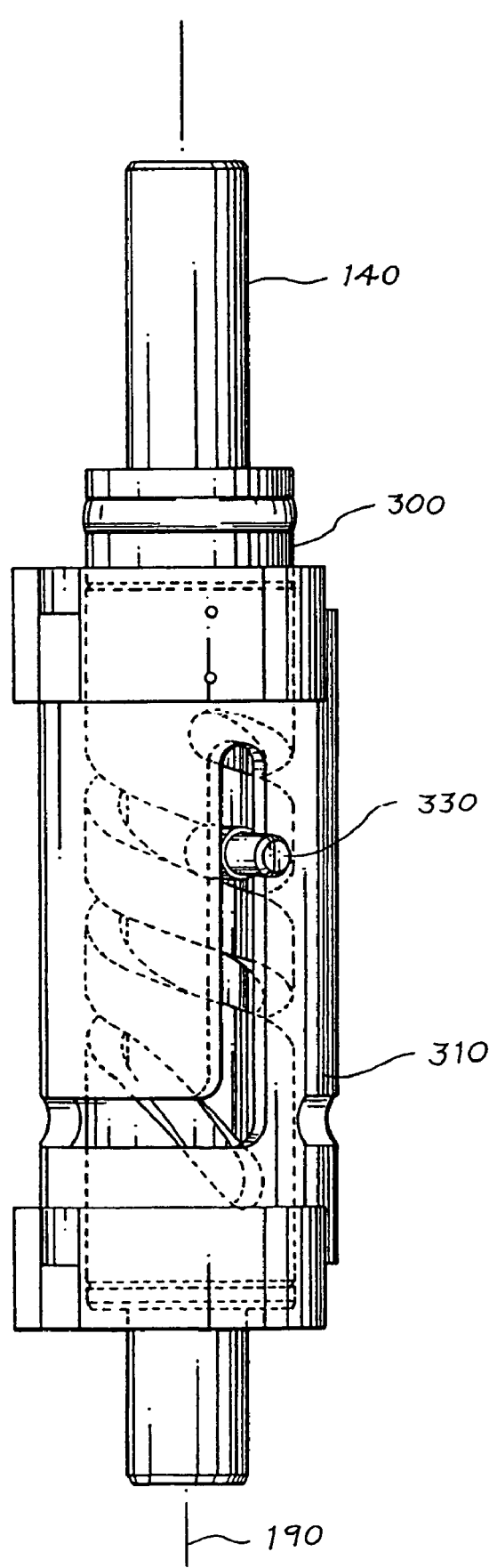
FIG. 5 is an illustration of a preferred embodiment in which the slots shown in FIGS. 4A-4D are wrapped around concentric cylinders.

In the implementation of this presently preferred embodiment, the sloped slots 200, 210 in FIGS. 4A-4D are wrapped around two concentric cylinders 300, 310 (see FIG. 5). Thus, slot 200 becomes a helical slot in annular cylinder 300, and slot 210 becomes an L-shaped slot in annular cylinder 310. In FIG. 5, the L-shaped slot is formed in the translucent exterior annular cylinder 310, and the helical slot is formed on the interior annular cylinder 300. Both slotted cylinders 300, 310 are allowed to rotate with respect to one another and with respect to the interior column 140, which contains the rotational axis 190 (see FIGS. 2 and 3). The slotted cylinders 300, 310 cannot translate with respect to one another but can both rotate and translate relative to the interior column 140. In the presently preferred embodiment shown in FIG. 5, a pin 330 is fixed rigidly to the interior column 140, which is stationary. The motion of the chamber 70 is rigidly coupled to the outermost cylinder 310 with the L-shaped slot. It is clear that the chamber 70 can rotate about axis 90 when the pin 330 is in the horizontal portion of the L-shaped slot and can translate vertically when the pin 330 is in the vertical portion of the L-shaped slot. Rotation of the cylinder 300 with the helical slot with respect to cylinder 310 causes the overall chamber 70 motion.

It should be noted that the slope of slot 200 in FIGS. 4A-4D, which translates into a helical slot in FIG. 5, controls not only the speed of the lift but also a mechanical force advantage in the raising and lowering of the chamber 70. In FIGS. 4A-4D, for a given horizontal force on slot 200, a vertical force is applied either upward or downward on the pin 220 depending on the direction of motion. Thus, slopes nearer the horizontal will provide higher vertical forces on the pin 200. In fact, the preferred embodiment shown in FIG. 5 uses two different slopes on the helical slot. The more gradual slope provides for mechanical advantage during the raising and lowering of the cylinder 300, and also reduces the speed of chamber 70 descent when closing the chamber 70. Slowing the chamber 70 descent speed is preferred to minimize soil and pressure disturbances above the soil prior to a flux measurement.

Figure 6:
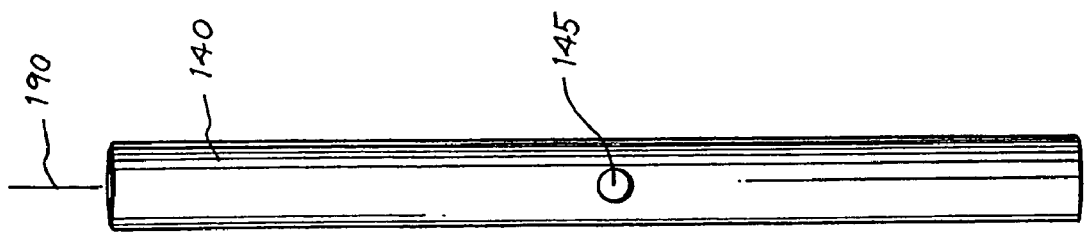
FIG. 6 is an illustration of an interior column of a lift-and-rotate mechanism of a preferred embodiment.

Returning to the drawings FIGS. 6-10 are illustrations showing the assembly of a lift-and-rotate mechanism 400 of a preferred embodiment. With reference to FIG. 6, the assembly starts with an interior column 140 (which is also referred to herein as a vertical shaft). The interior column 140 comprises the single vertical axis of rotation 190 for the lift-and-rotate motion. The interior column 140 also comprises a single horizontal hole 145, which serves as an attachment point for the main drive pin 330, which is described below. In a presently preferred embodiment, the interior column 140 is made of anodized aluminum, is 11 inches in length, and has an outer diameter of one inch. Also, the hole 145 is preferably 5.3 inches from the bottom of the interior column 140.

Figure 7:
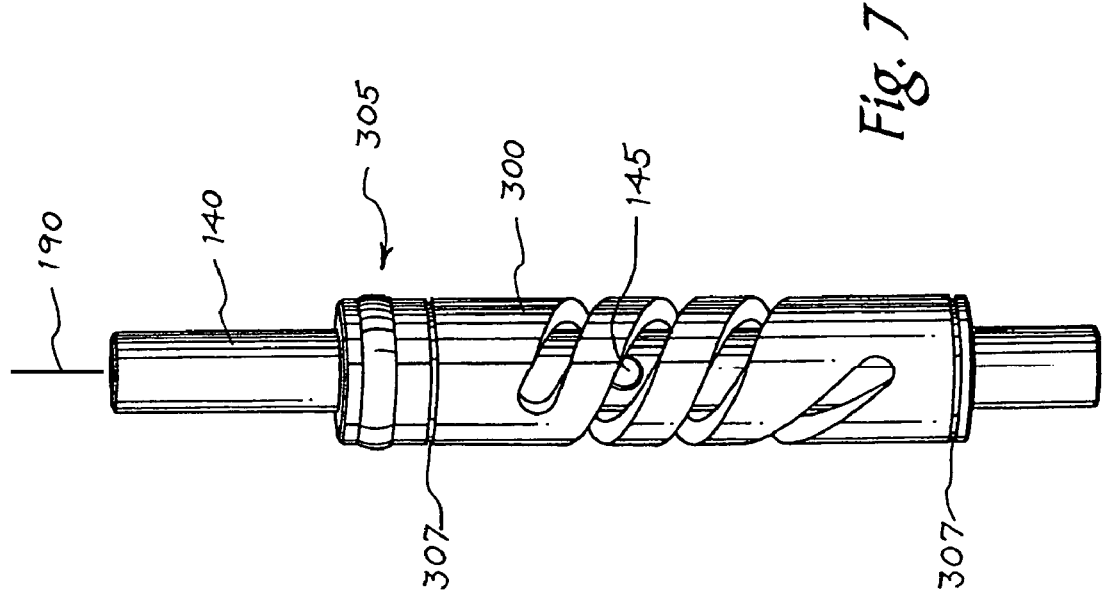
FIG. 7 is an illustration of a mid column installed around an interior column of a lift-and-rotate mechanism of a preferred embodiment.

In FIG. 7, a mid column 300 is installed around the interior column 140. The mid column 300 is an annular cylinder with a helical slot and is slid onto the interior column 140. The helical slot of the mid column 300 passes completely through the mid column 300, allowing a pin of appropriate diameter to be inserted completely through. The mid column 300 preferably has plastic sleeve bushings mounted to the interior diameter at either end. At the stage of assembly shown in FIG. 7, the mid column 300 can both rotate and translate up-and-down on the interior column 140. Near the top of the mid column 300 is a crowned area 305, which will serve as one of the pulleys in a belt drive mechanism. Incorporation of the pulley geometry into the mid column 300 reduces the part count and requires less assembly time than a separate drive pulley. Both ends of the mid column 300 contain grooves 307 which, when fitted with snap rings, will couple vertical loads to an outer column 310 (see FIG. 8).

The mid column 300 contains a segmented helical slot with two different lead angles of 20 and 45 degrees. The 20-degree lead angle is engaged during the lift phase of the motion, and the 45-degree lead angle is engaged during the rotate phase of the motion. The gentler 20-degree lead angle provides more lifting force during the lift phase of the motion than a steeper lead angle. However, lead angles shallower than 20-degrees may become problematic since there is preferably some minimum amount of material thickness between slots to maintain structural integrity of the mid column 300. The width of the slot remains constant to accept the main drive pin 330. In a presently preferred embodiment, 20-degrees is seen as the shallowest lead angle that can be achieved without degrading the structural integrity of the mid column 300. Also in a presently preferred embodiment, the mid column 300 is 7 inches in length and has an outer diameter of 1.75 inches (with an inner diameter that closely matches the outer diameter of the inner column 140). The slot width of the mid column 300 is preferably 0.4 inches.

Figure 8:
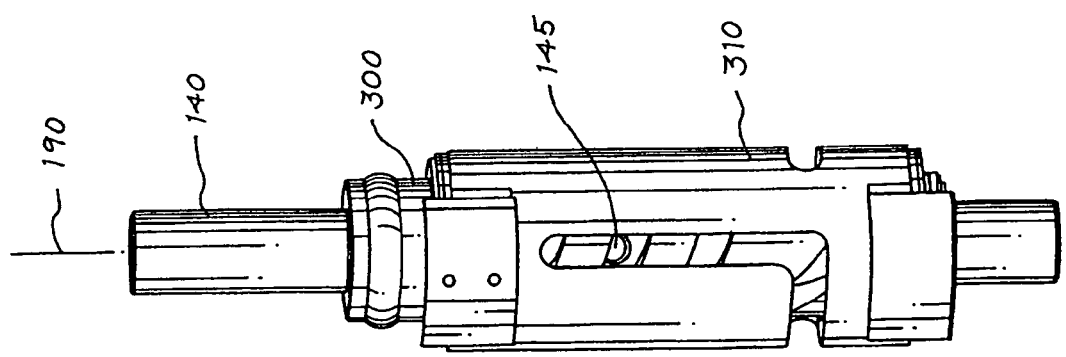
FIG. 8 is an illustration of an outer column installed over a mid column/interior column assembly of a lift-and-rotate mechanism of a preferred embodiment.

FIG. 8 is an illustration of an outer column 310 installed over the mid column 300. The outer column 310 can be slid onto the mid column 300. The outer column 310 is an annular cylinder with an L-shaped slot, with the L-shaped slot passing completely through the outer column 310. The L-shaped slot of the outer column 310 has both vertical and horizontal legs. Once the outer column 310 is slid into place, it is vertically constrained to the mid column 300 using flanged bushings (preferably, Igus), thrust washers, and snap rings, which fit into grooves of the mid column 300. At the stage of assembly shown in FIG. 8, the outer column 310 can rotate with respect to the mid column 300 but cannot translate vertically with respect to the mid column 300, and the mid column 300 and outer column 310 translate together. Also at this stage of assembly, the mid column 300 can rotate with respect to the interior column 140, and the mid column 300 and outer column 310 together can translate relative to the interior column 140. It is preferred that flange bushings be mounted in the inside diameter of the outer column 310, along with thrust washers and snap rings. These components are used to translate vertical forces from the mid column 300 to the outer column 310 while not impeding relative motion.

In a presently preferred embodiment, the outer column 310 has a length of 6.3 inches and an outer diameter of 2.5 inches. The vertical slot in the outer column 310 is preferably 3 inches (this allows for a three-inch vertical lift), and the horizontal slot is preferably 2.5 inches (this allows a 120-degree rotation).

Figure 9:
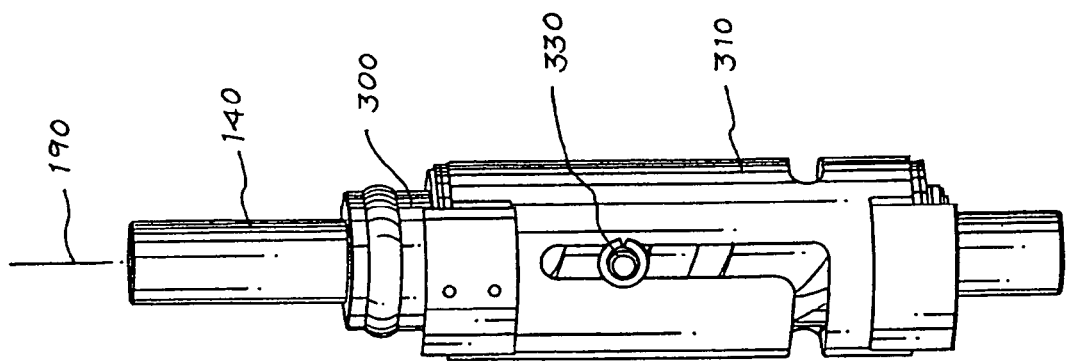
FIG. 9 is an illustration of a drive column assembly of a lift-and-rotate mechanism of a preferred embodiment.

The assembly in FIG. 8 is then secured together with a single drive pin 330, as shown in FIG. 9. This drive pin 330 passes completely through the L-shaped slot in the outer column 310, the helical slot in the mid column 300, and the single hole 145 in the interior column 140. The drive pin 330 thus uniquely locates the mid column 300 and outer column 310 with respect to the horizontal hole 145 in the interior column 140. The pin 330 is secured in place using two snap rings, which fit into grooves on either end of the pin 330.

In a presently preferred embodiment, the drive pin 330 is a 0.375 inches hardened steel pin (with a Rockwell C hardness of 63-65) and has two grooves, each 0.029 inches wide. Also, the outer diameter of the snap rings is preferably 0.61 inches. The mid column 300 and outer column 310 are hard-coat anodized with an impregnated PTFE (Nituff™ coating from Nimet Industries, Inc. in South Bend, Ind.). The exterior of the pin 330 and the interior of the grooves in both the mid column 300 and outer column 310 are wear surfaces since the pin 330 rides in the slots of the columns 300, 310. The initial intent is to use the Nituff™ coating and unlubricated components to eliminate the need for periodic lubrication. Should this prove infeasible, the main drive pin 330 and the slots of the mid column 300 and outer column 310 can be lubricated to reduce friction and noise that may result from sliding contact.

If the interior column 140 in FIG. 9 is held fixed, the assembly of the mid column 300 and outer column 310 is constrained to translate up-and-down when the drive pin 330 is in the vertical leg of the outer column 310 slot. Similarly, the outer column 310 is constrained to rotate about the interior column 140 and mid column 300 when the drive pin 330 is in the horizontal leg of the outer column 310 slot. Rotation of the mid column 300 with respect to the outer column 310 causes the drive pin 330 to move throughout the L-shaped slot of the outer column 310. Thus, aside from motorization, the core components of the lift-and-rotate mechanism 400 are now present in FIG. 9.

Figure 10:
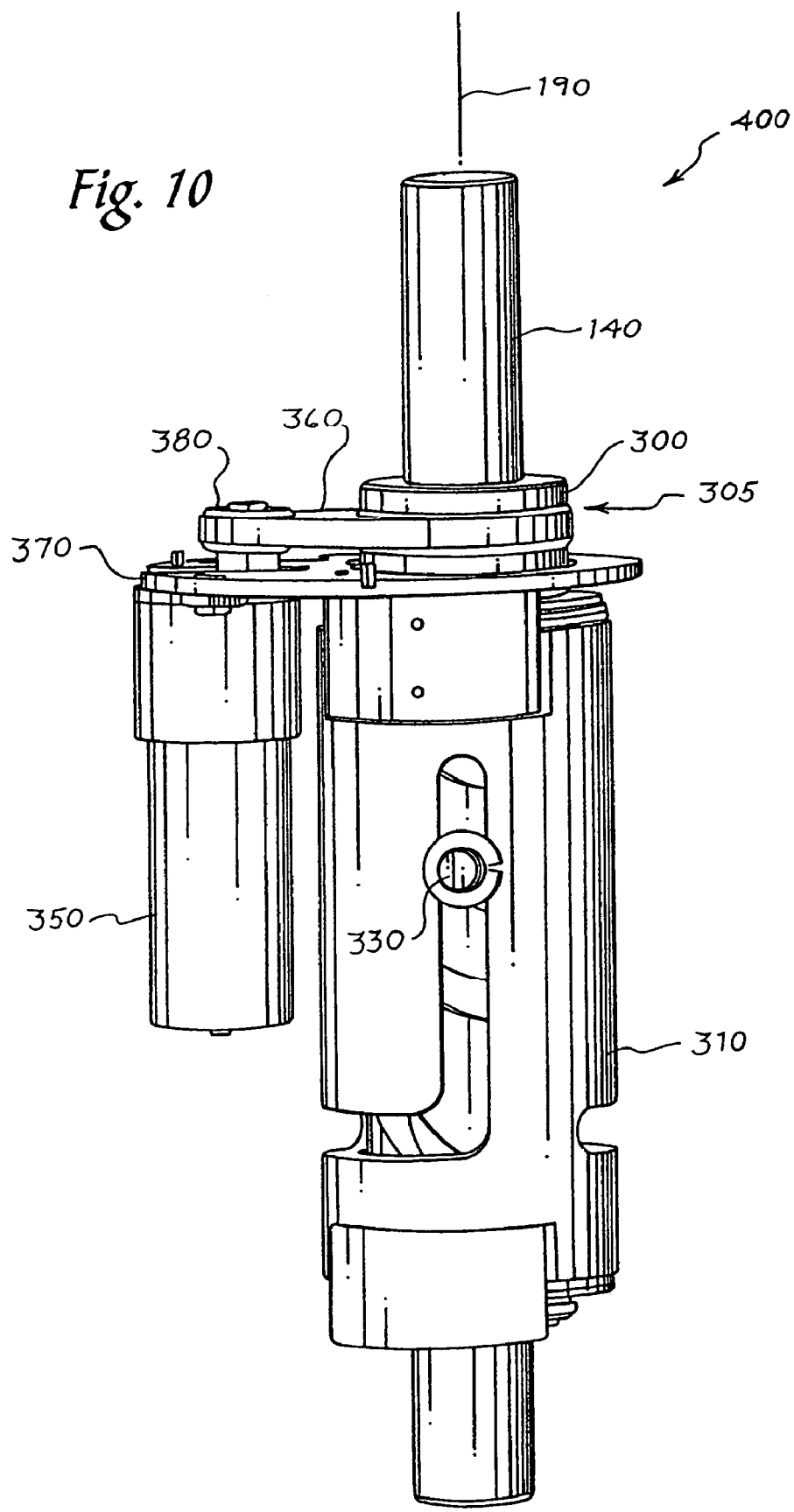
FIG. 10 is an illustration of a drive column assembly with a motor and belt of a preferred embodiment.

FIG. 10 shows the assembly of FIG. 9 with the addition of a DC gear-motor 350 and belt drive mechanism. The DC motor 350 is rigidly attached to the outer column 310 via a motor mounting plate 370, and a flat drive belt 360 connects the integrated crowned pulley 305 on the mid column 300 to a motor-mounted pulley 380. The motor 350 causes a relative rotation of the mid column 300 with respect to the outer column 310. During the lift phase of the motion, the mid column 300 rotates with respect to the outer column 310, and the outer column 310 translates vertically along with the mid column 300 with respect to the inner column 140. During the rotate phase of the motion, the mid column 300 remains stationary with respect to the inner column 140, and the outer column 310 rotates with respect to the inner column 140 and mid column 300. Referring back to FIG. 1, the chamber support structure 100 is rigidly coupled to the outer column 310. Thus, the lift-and-rotate motion of the outer column 310 is directly transferred to the chamber 70 through the chamber support structure 100.

In a presently preferred embodiment, the belt 360 is flat with 95-97% efficiency, made of polyethylene, and has a width of 0.25 inches and a length of 7.8 inches. A suitable belt can be purchased from SDP-SI. If a flat belt slips prematurely during the transition from lift to rotate motions, alternative flat belt drive geometries can be used. Alternative mechanisms can also be used, such as a chain-drive mechanism (two sprockets and a single chain) and a v-belt drive mechanism. Preferably, the pulley on the mid column 310 has a diameter of 1.75 inches, and the pulley coupled with the motor 350 has a diameter of 0.715 inches. Also in the presently preferred embodiment, the motor 350 has a gear ratio of 585:1. Suitable brushed DC gear motors can be purchased from Micromo, Pittman, and Globe.

By way of summary, the presently preferred embodiment described above incorporates the following features that are useful in maintaining low cost and reduced complexity of the lift-and-rotate mechanism while providing much of the same functionality as the more-complex LI-8100 Long-Term Chamber:

(1) The lift-and-rotate motion concept allows all of the moving components to be designed around a single vertical axis, offset horizontally from the sampling area. The mechanism necessary to produce the motion can be compactly designed around this vertical axis. In contrast, in the LI-8100 Long Term Chamber, motion is driven around two horizontal axes. The first horizontal axis is responsible for the bulk translation of the chamber to and from the sampling area, and the second horizontal axis is responsible for rotation of the chamber to maintain a downward facing orientation. The motions of these two axes are kinematically coupled through a drive chain. The lift-and-rotate concept allows all of the motion to occur about a single axis; namely, a single vertical axis. The single axis reduces the complexity of kinematically coupling multiple axes. The vertical nature of the axis allows the mechanism to have a minimal footprint on surrounding soil.

(2) The concentric column design decouples the lift phase and the rotate phase of the motion and allows the use of a rotary-gear motor. When contrasted with the linear lead-screw alternative described below, the concentric column design reduces the vertical height of the actuating mechanism by more than 40%.

(3) The concentric cylinder design allows both the lift and rotate phases of the motion to be accomplished by a single motor driven at constant speed. The speed of the lift phase can be controlled both through the motor speed, the pulley size ratios, and the helical lead angle of the mid-drive column. The speed of the rotate phase is controlled only by the motor speed and the pulley size ratios. Thus, the designer can choose the rotate speed by selecting a motor speed and pulley size ratio and can then tune the lift speed by varying the helical lead angle. There is a tradeoff with mechanical advantage, as steeper helical lead angles increase the lift speed but subsequently decrease the lift force for a given motor torque. The presently preferred embodiment uses a helical lead angle of 20 degrees for the lift phase and a helical lead angle of 45 degrees for the rotate phase.

(4) A compliant coupling between the chamber and the chamber support structure allows nearly the same sealing force to be applied to the chamber for a range of positions of the support structure. This allows simple end-point positional on-off control of the lift-and rotate mechanism while maintaining nearly a constant sealing force at the chamber. Conversely, a rigid chamber support structure would require precise positional control of the lift-and-rotate mechanism in order to maintain a constant downward sealing force at the chamber.

(5) The end-point on-off positional control is preferably accomplished using two Hall-effect limit switches located at either end of travel. When an open command is received from a master controller, the motor is driven in the open direction at constant speed until a limit switch is reached. Similarly, when a close command is received from a master controller, the motor is driven in the close direction at constant speed until the closed limit switch is reached. The limit switch function could be similarly accomplished with mechanical switches, optical interrupt switches, or Hall-effect switches. The design uses Hall-effect interrupt switches (preferably, a Honeywell SR17C-J6 switch) to provide a lifetime far beyond that of mechanical switches while avoiding the dust/contamination sensitivity of optical interrupt switches.

(6) The vertical and rotational loads are transferred from the two slotted drive columns to a single drive pin. The design uses a lubricated pin in sliding contact with the mating slots. The sliding-contact design eliminates the need for rolling contact bearings or bushings, subsequently reducing system complexity and cost.

(7) The concentric drive cylinder design allows for the use of small plastic bushings (preferably from Igus, East Providence, R.I.), which are less expensive and more debris tolerant than conventional ball bearings. Moreover, the plastic bushings can provide for both radial and thrust loads like a ball bearing without the complexity and cost of the ball bearing. The use of bushings rather than bearings further reduces the size of the mechanism since rolling-element bearings have larger outside diameters than a bushing for the same inside diameter.

(8) The use of a belt coupling between the drive motor and the mid column allows the mechanism to slip should the chamber or chamber support structure come into contact with an obstacle. The slip is a self-protection mechanism that prevents damage to the device or external object should a significant obstacle be encountered. The point at which the belt slips can be coarsely adjusted (during manufacture) by varying the belt tension. Self protection is also incorporated by monitoring the drive motor electrical current and shutting off motor current should it exceed a predefined value.

There are several alternatives that can be used with these embodiments. For example, in the embodiment shown in FIG. 1, the height of the cylindrical enclosure 150 exceeds the height of the sampling chamber 70, which can negatively affect the vent 90. The sampling chamber 70 is equipped with a vent 90 to allow pressure equalization between the interior and exterior of the chamber 70. The vent mechanism 90 relies on certain air-flow patterns to function as designed. If the cylindrical enclosure 150 has an impact on air-flow patterns around the vent 90 (e.g., if the cylindrical enclosure 150 produces non-uniformities in air-flow that may adversely affect the vent's 90 capability to equalize pressure inside and outside the chamber 70), the height of the cylindrical enclosure 150 can be reduced or the vent 90 can be relocated to a less affected area.

Also, in the embodiment shown in FIG. 1, cables (e.g., electrical signal and power cables) are routed to the lifting-and-rotating cylindrical enclosure 150. Accordingly, these cables are lifted and rotated with the mechanism. If the cables catch and bind on surrounding objects during chamber motion, a track or enclosure can be used to manage the cables to remove the potential for catching and binding. Further, instead of using a DC motor, other mechanisms can be used, including, but not limited to, pneumatic bellows and hydraulics. Further, instead of using a single motor to perform both the translational and rotational moving, two motors can by used—one for each type of movement.

The preferred embodiment described above uses a fixed-pin geometry, and the primary lift-and rotate mechanism along with circuit boards, the enclosure, motor, etc are all moved up and down around the main drive pin. While this geometry may be the easiest geometry to seal, an alternative geometry based on the same mechanical principal can be used. In this alternative, the rotating cylinders are fixed, and the interior shaft is allowed to perform the rotation and lift. This alternative would eliminate the moving cables issue described above. Further, this alternative would reduce the moving mass of the system, thereby decreasing the torque requirements for the motor and improving overall mechanical efficiency. For these reasons, it may be preferred to use this fixed-cylinder-geometry alternative over translating/rotating cylinder geometry described above.

In another alternative, a linear actuator is used instead of using the rotational gear-motor described above. (As discussed above, a sprocket/chain drive mechanism and a v-belt mechanism can be used.) Examples of commercial off-the-shelf linear actuators are the Hybrid Linear Actuator, Size 23 External 57000 Series and the Hybrid Linear Actuator, Size 17 External 43000 Series from Haydon Switch and Instrument (HSI), Waterbury, Conn. (USA). A linear actuator comprises a lead screw integrated with a lead nut and a motor. The linear actuators from HSI mentioned above utilize stepper motors rather than brushed DC motors. In operation, the linear actuator would be vertically mounted in a vertical annular cylinder, with the axis of the cylinder and the axis of the lead screw being concentric. The cylinder would have two diametrically opposed slots through which a horizontal pin would pass, from one side of the cylinder through the opposing side. This pin would be rigidly attached to the lead nut of the motor and would be constrained to move in the slots cut in the cylinder. The slots would have a vertical portion which accomplishes the lift phase of the lift-and-rotate motion. Thus, the motor would lift the pin vertically in the slot, and this pin motion would be directly transferred to the chamber.

The rotate phase of the motion is accomplished by turning the vertical slot, after a prescribed lift distance, into a helical slot about the cylinder's axis. The helical slot would cause the pin to rotate about the cylinder axis as it translated vertically, being pushed or pulled by the linear actuator. A large helical lead angle would cause the pin to rotate slowly during an upward or downward translation. A smaller helical lead angle would cause a larger rotation for the same translation. There are also mechanical-advantage considerations when selecting an appropriate lead angle.

An advantage of this alternative is that half of the mechanism could be purchased as an assembly directly from HSI. There are significant cost savings to the purchase of this integrated assembly versus purchasing component parts. However, in this alternative, vertical translation achieves the rotate phase. Without vertical translation, there is no mechanism to achieve rotation here. Helical lead angles near 45 degrees can be used for speed and mechanical advantage. However, at these helical lead angles, the mechanism may become very tall. Since the height of the mechanism can potentially shade the sampling area, drive size and weight, and potentially interfere with air-flow patterns around the chamber vent, the rotational gear-motor embodiment described above is preferred. By using a rotational gear-motor instead of a linear actuator, the preferred embodiment described above allows a decoupling between the lift phase and rotate phase of the motion. The rotate phase no longer requires the vertical translation required in the linear actuator alternative. Thus, the preferred embodiment described above minimizes the height of the drive column by decoupling the lift phase and rotate phase and accomplishes both motions with only a single drive motor running at constant speed.

Referring now to FIGS. 11-18, an alternative embodiment of a gas flux chamber with a lift-and-rotate mechanism is shown. This embodiment operates in largely the same manner as the embodiments disclosed above, with a few exceptions that are described below, and offers many of the same advantages and benefits as the embodiments discussed above. For components disclosed in FIGS. 11-18 that correspond to components disclosed in FIGS. 1-10, corresponding reference numerals are used.

Figure 11:
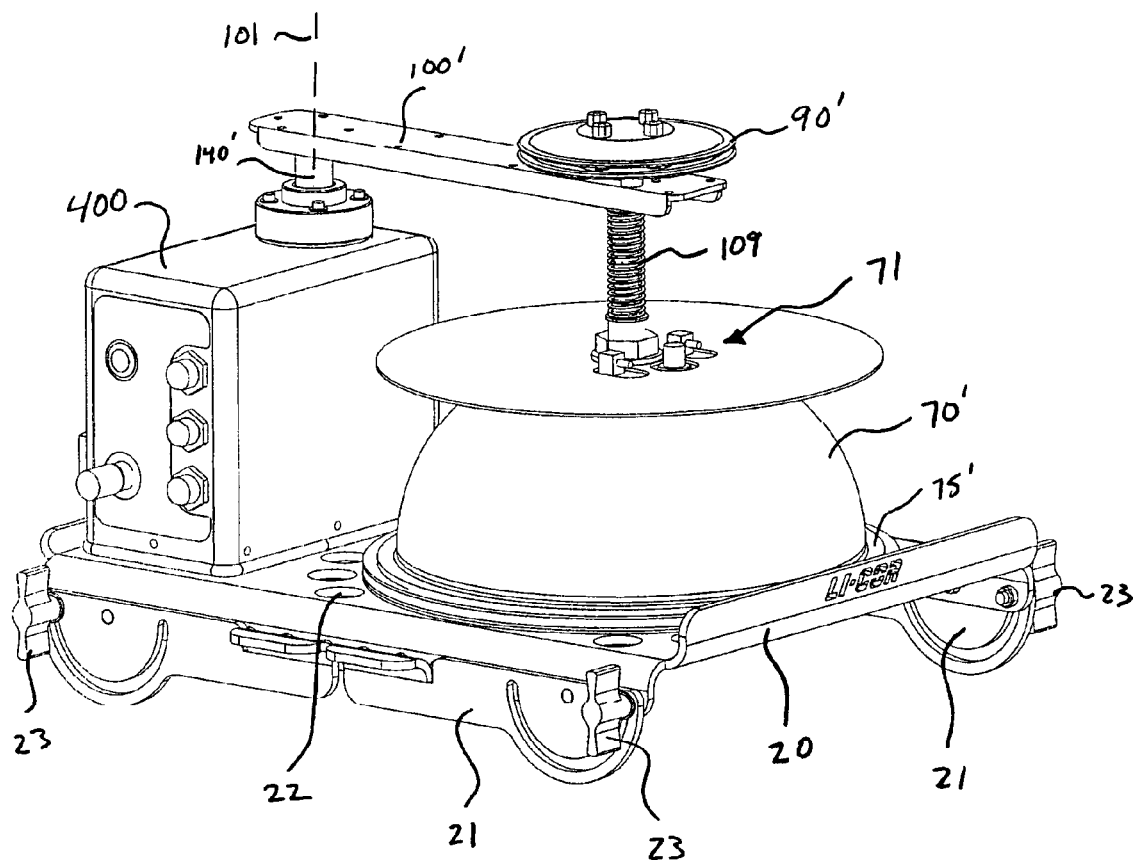
FIG. 11 is an illustration of a gas flux chamber assembly of a preferred embodiment in which a chamber is in a first, closed/sampling position.

By way of overview, FIG. 11 shows an assembly 10' that includes a base plate 20', which includes a plurality of feet 21 that can be moved or removed by use of the thumb screws 23. In use, the base plate 20' is preferably placed on the ground or other surface near the area that is to be sampled or tested. The base plate 20' preferably includes a number of perforations 22 that serve to minimize the base plate's impact on gas flux and sunlight/rain penetration around the sample area. In addition the vertical edges of the base plate 20' can be perforated to reduce the impedance to gas diffusion introduced by the base plate 20'.

The assembly 10' also includes a chamber 70'. When the chamber is in the closed or sampling position, the chamber 70' resets on a collar 75' that is attached to the base plate 20' and that can include a gasket or other sealing mechanism. A vent 90', such as the one described above, is coupled with the chamber 70' that maintains the ambient surface pressure within the chamber 70', as described above. The chamber is coupled with a support structure 100', such as an arm, which enables the chamber to be moved, as described herein. A spring 109 can be used to assist in the connection of the chamber 70' and the support structure. A gas analyzer (not shown) can be coupled with the chamber via gas inlets and outlets 71 to enable the gas analyzer analyze or sample the area contained by the chamber 70'.

The assembly 10' also preferably includes a housing 400 that generally encloses a lift-and-rotate mechanism. In a preferred embodiment, a portion of the interior column (described below) is allowed to extend outside of the housing 400 for connection to the support structure 100'. The housing 400 is preferably water-tight, which makes it weather proof for the components contained within the housing 400. The combination of the height of the housing 400, the height of the support structure 100', and the position of the vent 90' allow for the vent 90' to be positioned higher than the housing 400 and the support structure 100'. This minimizes the impact of the lift-and-rotate mechanism and its enclosure on air-flow patterns in and around the vent 90'. This results in a more efficient and effective vent 90' and also results in more effective and accurate analyses on the sample.

Figure 12:
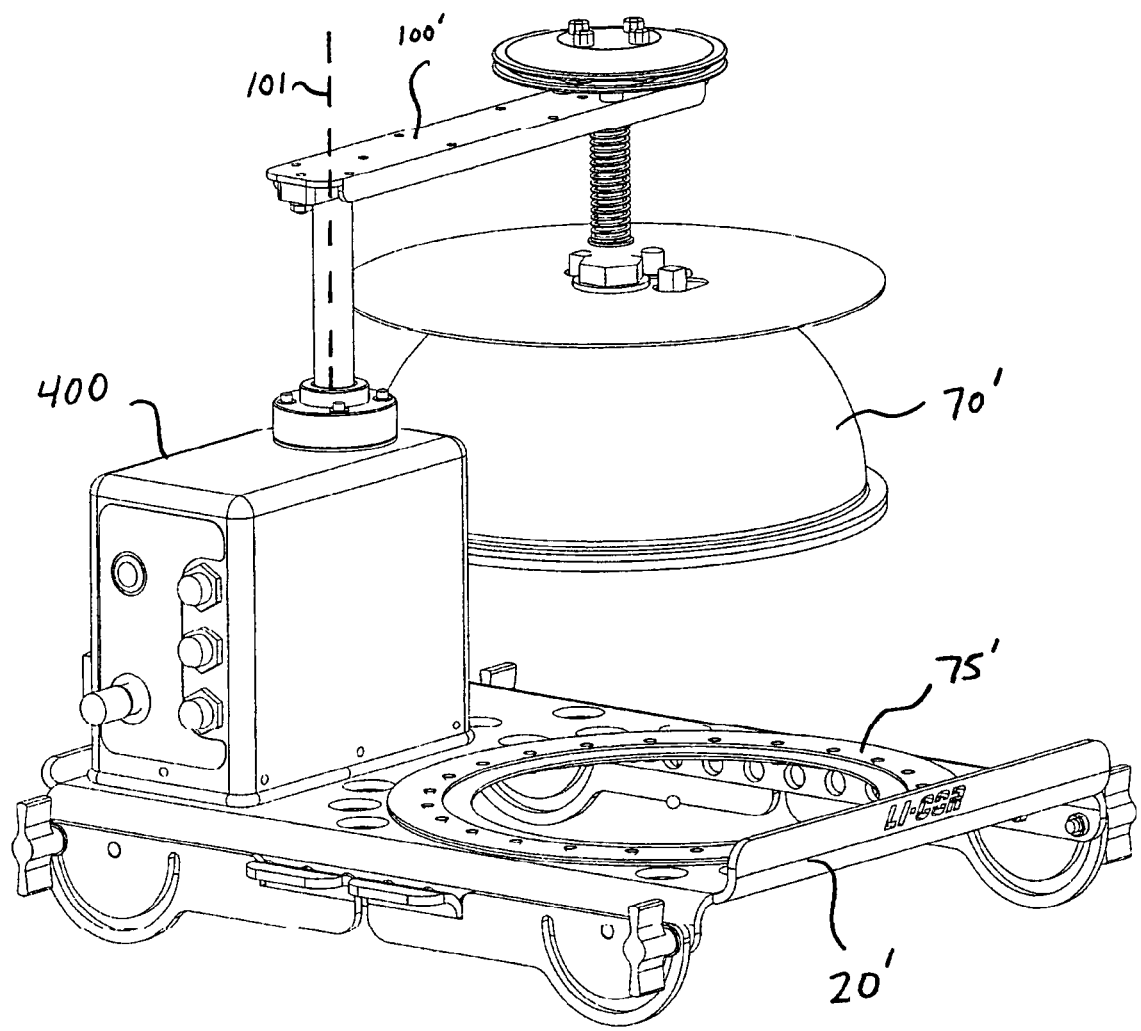
FIG. 12 is an illustration of a gas flux chamber assembly of a preferred embodiment in which a chamber is shown in one example of a second open/rotated position.
Figure 13:
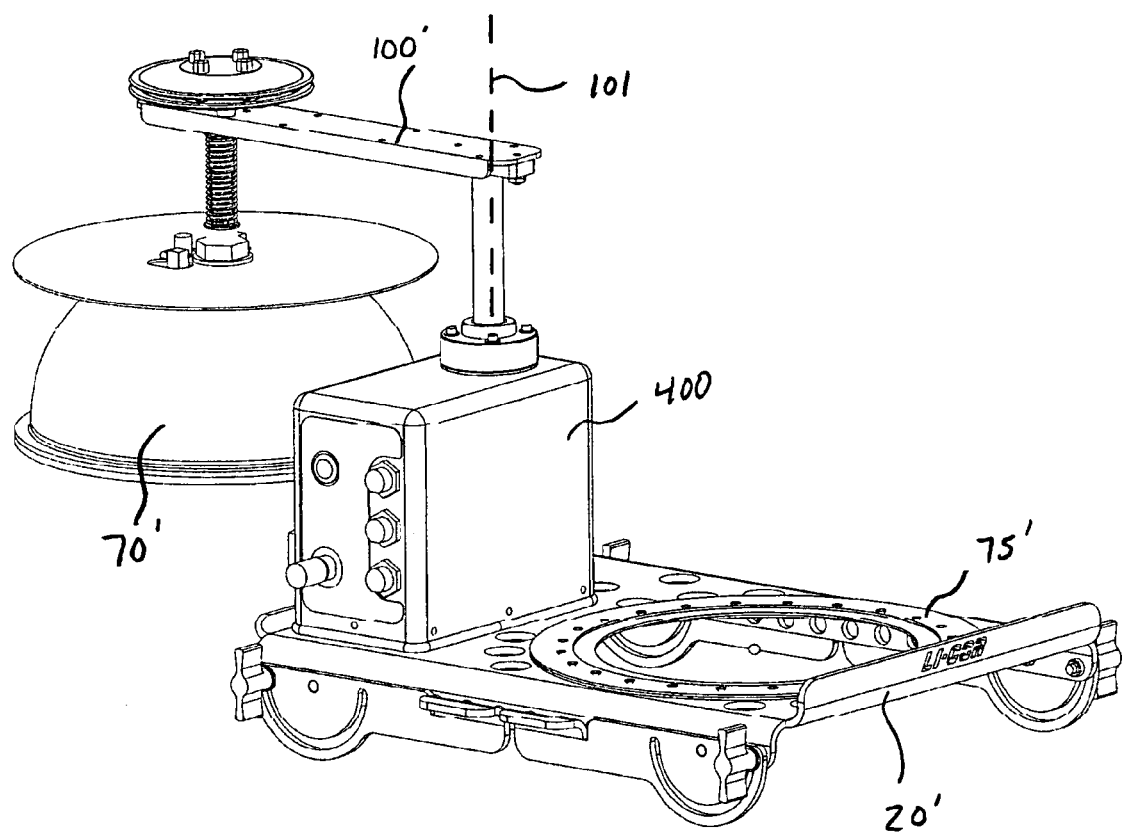
FIG. 13 is an illustration of a gas flux chamber assembly of a preferred embodiment in which a chamber is shown in another example of a second open/rotated position.

Referring now to FIG. 12, the gas flux chamber disclosed and described in conjunction with FIG. 11 is now shown in a first open position. In this position, the chamber 70' has been lifted off of the base plate 20' and the collar 75' and has been rotated to a position outside of the area over the sample. Actuation of the lift-and-rotate mechanism contained within the housing 400, and described in more detail below, has caused the support structure 100' to lift-and-rotate, thereby causing the chamber 70' to also lift and rotate about an axis 101. Similarly, FIG. 13 shows the same gas flux chamber wherein the chamber 70' has been rotated to another open position where the chamber 70' is outside of an area above the sample. In this figure, the support structure 100' has been further rotated about the axis 101 thereby causing the chamber 70' to be similarly rotated, approximately 180 degrees from the closed or sampling position. As both the support structure 100' and the chamber 70' rotate and move with respect to the base plate 20', as shown in FIGS. 11-13, the housing 400 and certain portions of the lift-and-rotate mechanism remain fixed with respect to the base plate 20', as described in more detail below. This results in a decrease in the size and weight of the parts and components that are moved when the chamber 70' is lifted and rotated. This also allows cables and cords, such as electrical, signal, and power cables and cords, which can be connected to the housing 400, to remain in a constant position when the chamber 70' is lifted an rotated.

Figure 14:
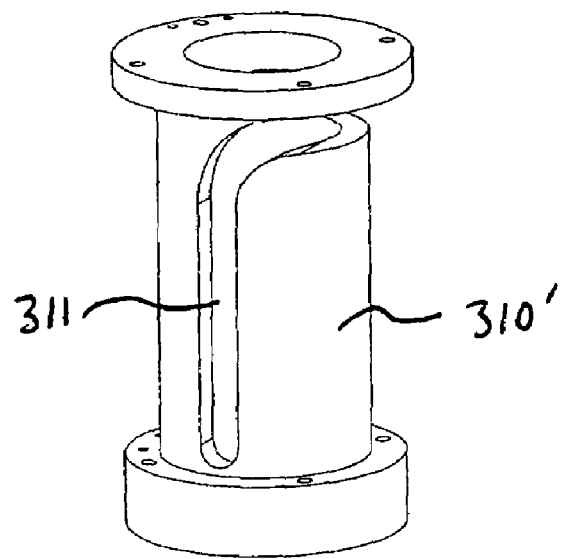
FIG. 14 is an illustration of an outer column of a lift-and-rotate mechanism of a preferred embodiment.

Referring now to FIGS. 14-17, various components of a drive column assembly of a lift-and-rotate mechanism are shown. FIG. 14 shows an outer column 310' of a drive column lift-and-rotate mechanism of a preferred embodiment. The outer column 310' preferably includes a generally L-shaped slot 311. The use of a single L-slot allows the horizontal portion of the L-slot to sweep out 180 degrees or more around the circumference of the annulus. The outer column 310' is preferably affixed to or coupled with the base plate 20' such that it does not move with respect to the base plate 20'.

Figure 15:
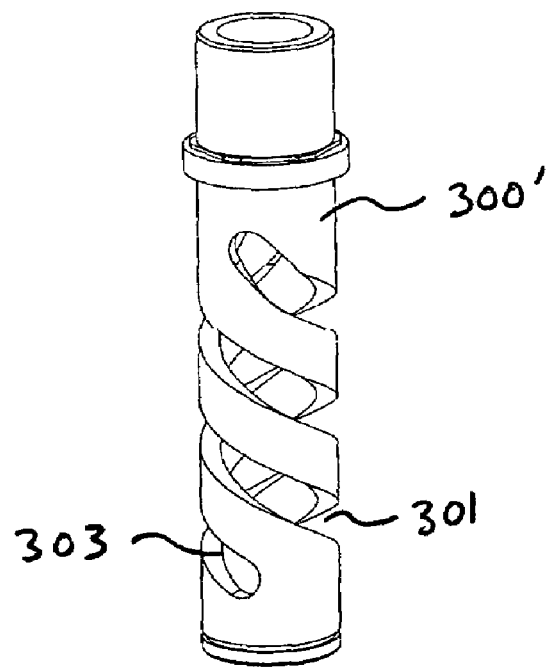
FIG. 15 is an illustration of a mid column of a lift-and-rotate mechanism of a preferred embodiment.
Figure 17:
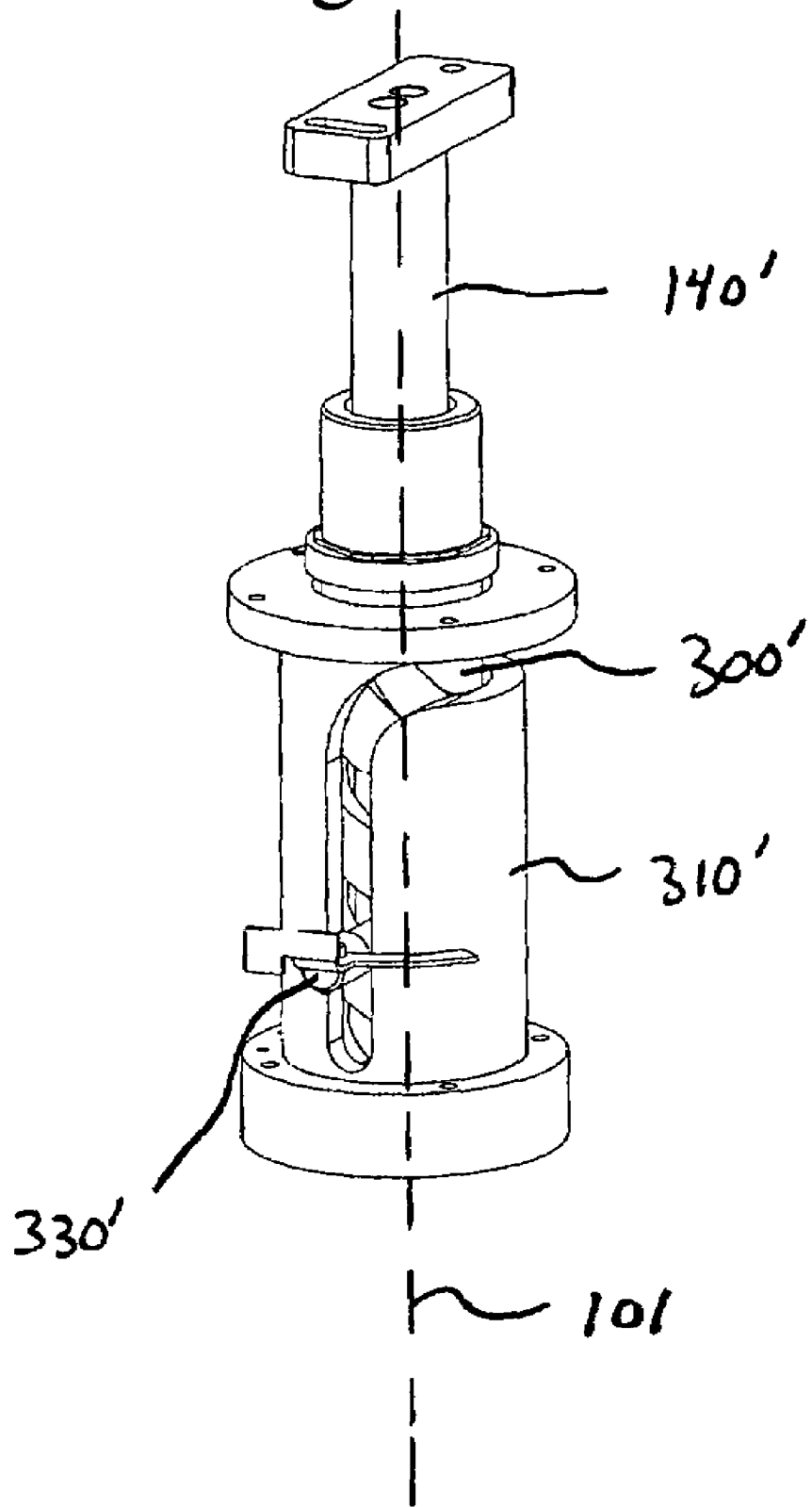
FIG. 17 is an illustration of a drive column assembly of a lift-and-rotate mechanism of a preferred embodiment.

FIG. 15 shows a mid column 300' of a lift-and-rotate mechanism of a preferred embodiment. The mid column 300' preferably includes a plurality of helical slots 301, 303. In a preferred embodiment, the plurality of helical slots 301, 303 comprise two diametrically opposed helical slots cut into an annular cylinder. The helical lead angle of the slots preferably increases near the top of the slots, which coincides with the transition between lift and rotate phases of motion. As shown in FIG. 17, the mid column 300' is placed within the outer column 310'. The mid-column 300', when assembled with the outer column 310' as shown in FIG. 17, is allowed to rotate about its own axis with respect to the fixed outer column 310', but is not allowed to translate.

Figure 16:
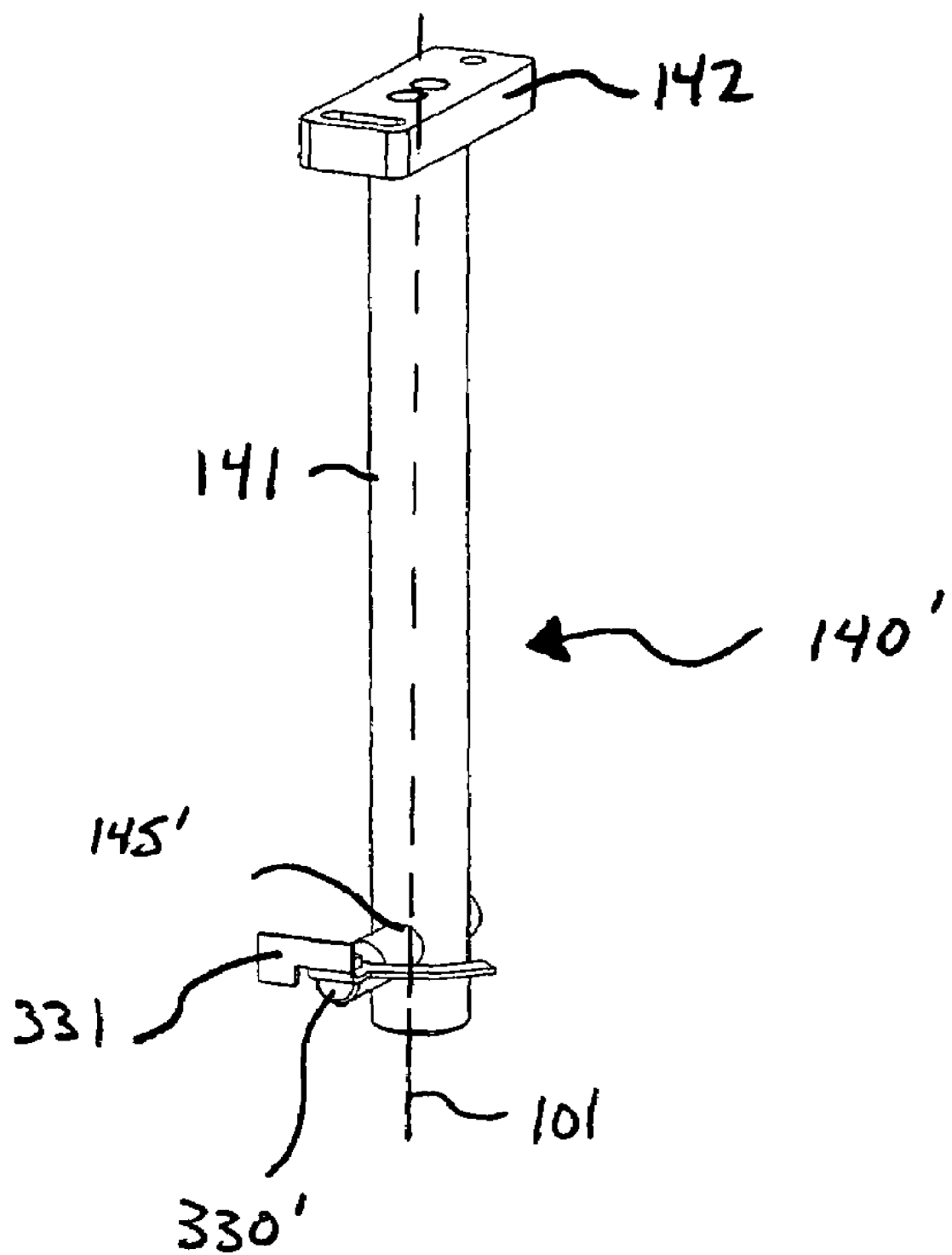
FIG. 16 is an illustration of an interior column of a lift-and-rotate mechanism of a preferred embodiment.

FIG. 16 is an illustration of an interior column 140' of a lift-and-rotate mechanism of a preferred embodiment. The interior column 140' preferably includes a cylindrical shaft 141, a top-mounted flange 142, which preferably connects to the chamber support structure 100', a pin 330' near the bottom, which is inserted into a hole 145' and actuates the interior column 140', and a small flag 331 attached to the pin 330', which can actuate Hall-effect sensors at both open and closed positions. When assembled as shown in FIG. 17, the interior column 140' is allowed to both rotate and translate with respect to the mid-column 140'. Preferably, the interior column is allowed to rotate about an axis 101 and translate along the axis 101.

As shown in FIG. 17, the interior column 140' can be placed within the mid column 300' and the pin 330' can be inserted through the L-shaped slot 311 on the outer column 310', through the helical slots 301, 303 in the mid column 300' and into the hole 145' in the interior column 140' to form a drive column assembly.

Figure 18:
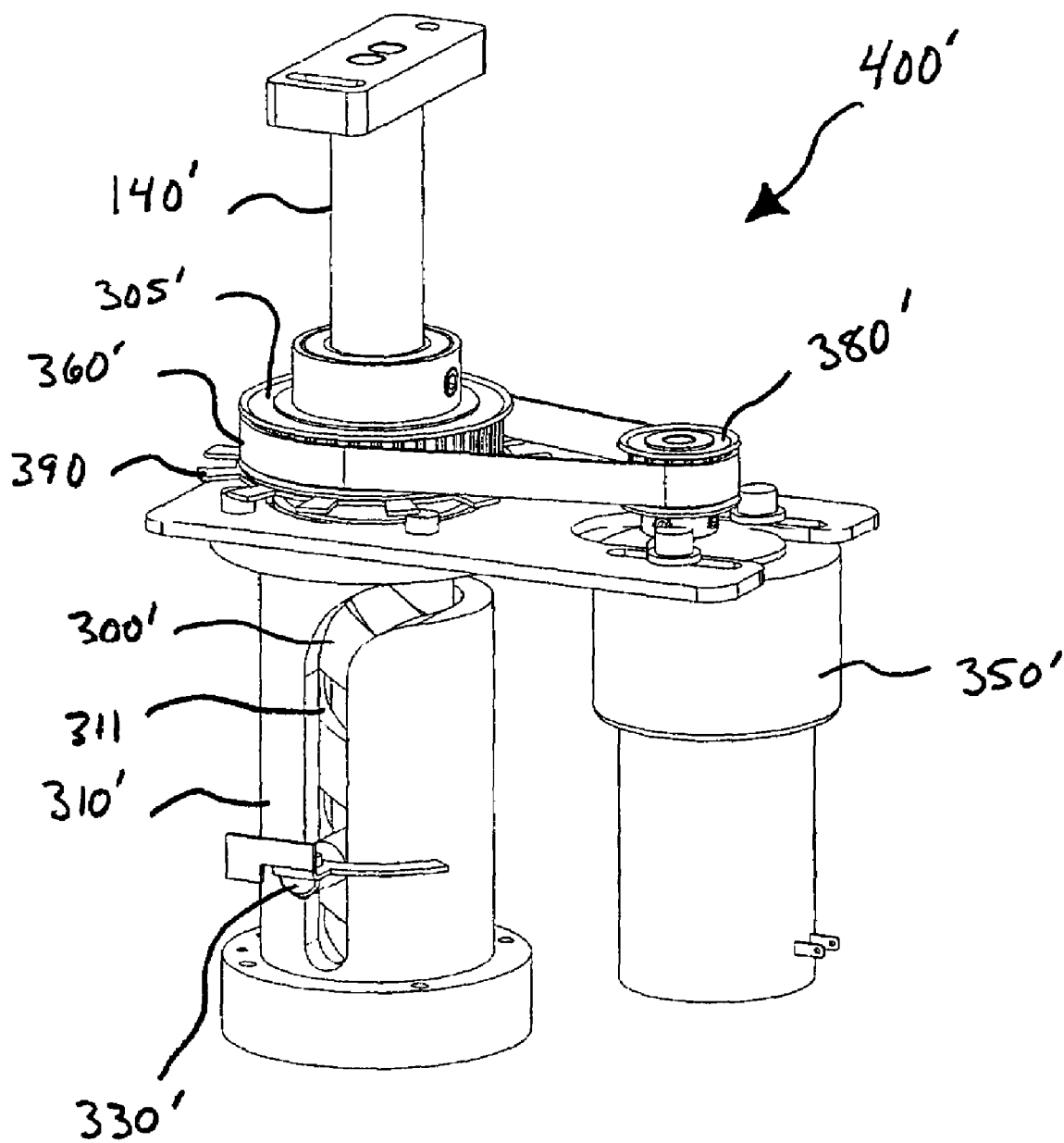
FIG. 18 is an illustration of a drive column assembly with a motor and belt of a preferred embodiment.

FIG. 18 is an illustration of a lift-and-rotate mechanism 400' of a preferred embodiment that includes a drive column assembly with a motor 350' and belt 360' of a preferred embodiment. As is shown in FIG. 17, FIG. 18 shows the outer column 310', the mid column 300' located within the outer column 310', and the interior column 140' located within the mid column 300'. The pin 330' has been inserted through the L-shaped slot 311 on the outer column 310', through the helical slots 301, 303 in the mid column 300' and into the hole 145' in the interior column 140' to form a drive column assembly. This assembly is designed to rigidly fix the majority of the components and electronics to the base plate 20' (FIG. 11). The interior column 140' is the primary moving element of the assembly. This interior column 140' lifts (translates) and rotates, while the mid-column only rotates 300', and the outer column 310' remains fixed to the base plate 20' (FIG. 11). The chamber 70' (FIG. 11) and its supporting structure 100' (FIG. 11) are attached to the interior column 140', and thus lift and rotate along with the interior column 140'. This greatly reduces the moving mass of the mechanism, as compared with the embodiments disclosed in FIGS. 1-10, thereby conserving actuation energy. Moreover, since key components in the embodiments shown in FIGS. 11-18 are stationary, all external cable connections remain stationary during chamber actuation.

FIG. 18 also shows a gear motor 350', two timing belt pulleys 305', 380', a timing belt 360', and a toothed wheel 390. The timing belt 360' and pulleys 305', 380' are preferably of Type GT2, 5 mm pitch, available from the Gates Corporation. The gear motor is preferably a Globe Motors Part Number 455A102-2 with a reduction ratio of 128:1. The timing belt 360' maintains the efficiency of a belt design (typically more energy efficient than gears), and eliminates any potential slip between the gear motor and the driven mechanism. The toothed wheel 390 is used to determine position feedback, as described herein.

The gear motor 350' causes the mid column 300' to rotate with respect to the fixed outer column 310', via the timing belt 360'. Rotation of the mid-column 300' causes the pin 330', and consequently the interior column 140', to translate upward in the vertical portion of the outer column L-slot 311. This is the lift phase of the lift-and-rotate motion. The vertical translation of the interior column 140' transitions to a rotation of the interior column 140' about its own axis 101 as the pin 330' nears the top of the vertical portion of the L-slot 311. During this rotation, the pin 330' follows the horizontal segment of the L-slot 311. This is the rotate phase of the lift-and-rotate motion. The outer column L-slot 311 has a large radius transitioning between the vertical and horizontal portions of the L-slot. This large radius helps smooth the transition between the lift and rotate phases of motion. The radius is also forgiving of slight misalignments between the transition point in the helical lead angles and the transition from horizontal-to-vertical in the L-slot 311. The interior column 140' will continue to rotate until it reaches a predetermined stopping point or open position. As described herein, the open position of the chamber 70' can be programmed by the end user between 0 degrees (directly above the sampling area) to 180 degrees, as shown in FIG. 13. The mid-column 300' and the outer-column 310' are preferably coated with a simple hard-coat anodizing in accordance with MIL-A-8625E, Type III. The pin 330' and slots 301, 303, 311 are preferably lubricated with Nye Lubricants Type 368A grease.

A microcontroller (not shown) is preferably used in conjunction with the gas flux chamber to, among other things, control the operation of the gear motor 350'. The microcontroller preferably dynamically measures motor current during all phases of motion. Should the mechanism encounter a significant obstacle, the motor current will increase, and if the motor current exceeds a predefined threshold, the microcontroller can stop applying voltage to the gear motor thereby stopping or aborting the movement. Preferably, the microcontroller will wait a predefined number of seconds, and then re-attempt to complete the move that was stopped or aborted. After a number of re-attempts, such as 4 unsuccessful retries, the microcontroller can cease trying to move the mechanism. Sensing motor over-current prevents the gear-motor 350' from damaging its integrated gear-box, and prevents the drive mechanism and exterior chamber components from unintentional damage due to collision with obstacles. The over-current sensing also provides a degree of personnel protection during the rotate phase of motion.

The inclusion of the toothed wheel 390 and, preferably, three Hall-effect sensors (not shown), allows for a more sophisticated position feedback system. The third Hall-effect sensor generates pulses as the toothed wheel 390 passes by. The toothed wheel 390 is rigidly coupled to the mid-column 300' as shown in FIG. 18. The microcontroller uses pulses generated by the toothed wheel 390, along with knowledge of motor rotation direction, to track the position of the mechanism throughout its entire range of motion. The use of a Hall-effect sensor and a ferrous toothed wheel is a fundamental and reliably way for determining position feedback. However, other types of devices, such as optical encoders, and more specifically Quadrature incremental encoders, could also be used to determine position.

The existence of position feedback enables several capabilities which are useful to the end user: (1) mechanism acceleration/deceleration; (2) endpoint programmability; and (3) park functionality. The control system is preferably programmed to gradually ramp the voltage applied to the gear motor 350', rather than apply it in a step-wise fashion. Ramping the voltage provides a smoother acceleration, and a more controlled external appearance. However, various other types of motor control, including the use of a step-wise motor control can be used. Deceleration based on position feedback can also be implemented in the control system. The lift-and-rotate concept allows the chamber 70' to be lifted from the collar 75' and rotated away from the collar 75' to a predetermined open position. The current mechanism allows open positions between 0 (directly above the collar 75') to 210 degrees. Open positions greater than 210 degrees are possible, but 210 degrees was chosen a preferred maximum to maintain structural integrity of the outer column. In order to provide adequate stopping distances, the practical limitations of the current design are between 0 and 180 degrees, with the motion between 180 and 210 degrees used as an uncontrolled deceleration zone. Various other configurations for opening positions can also be used.

An input device, such as pushbutton switch, can be included on the device 10', such as on the housing 400, to enable a user to locally open and close the chamber 70' by actuating the pushbutton. Actuation of the pushbutton can also cause the chamber microcontroller to be placed in a programming mode. The programming mode can be used to define the open position, at any one of a number of predefined positions between 0 and 180 degrees. Once placed in the programming mode, the chamber 70' moves to the open position last programmed. Clicks of the pushbutton cause the chamber to move approximately 36 degrees to the next available open position. Thus, the user is able to program the open position between 0 and 180 degrees in a finite number of discrete choices. In the presently preferred implementation, 6 position set-points were selected that are evenly spaced, approximately 36 degrees apart. However, virtually any number of set-points positioned any varying degrees could be used instead. Depending on the user's final application, there may be obstructions located in and around the chamber which would preclude a full 180 degree opening. The user is given ultimate flexibility of choosing the open position setting of the lift-and-rotate device. The programmed position is preferably maintained in non-volatile memory, such that the device remembers the programmed open-position with or without applied power. Other types of memory, including volatile memory, can be used to store the program data.

A significant advantage of the lift-and-rotate mechanism described herein is that it is self-locking in both open and closed positions. No motor power is required to maintain the chamber position against external loading (primarily gravity). This is extremely advantageous in remote locations where electrical power is scarce. In these remote locations, the energy source is often solar panels with battery storage, and energy conservation is critical. One disadvantage of the self-locking mechanism is the continuous compression of a chamber gasket when the chamber 70 is in the full-closed or sampling position.

The chamber 70' is typically shipped and stored in a position which is closed or very nearly closed. The closed position provides the most compact configuration for transport and shipping. However, a fully closed position compresses a gasket between the chamber 70' and the base plate 20'. This compression is necessary during normal operation to affect a gas-tight seal between the chamber 70' and base plate 20'. However, as with nearly all elastomers, the gasket is susceptible to creep under load and a phenomenon known as permanent set. When elastomers are deformed for extended time periods, they may recover less and less of their original shape. This permanent or nearly permanent change to the original shape is known as permanent set. Permanent set reduces the sealing efficacy of the gasket. Leaving the chamber in the fully closed position for extended time periods can result in gasket permanent set, and a consequent decrease in gasket efficacy. In order to avoid the negative impact of long-term gasket compression, a PARK function has been introduced. The PARK function is activated by double-clicking the pushbutton on the assembly 10'. Once the PARK function is activated, the chamber 70' moves to its fully closed position. The chamber 70' then moves a small amount in the open direction to a predefined position known as the PARK position. The PARK position is defined as open enough to relieve full compression on the chamber gasket, yet closed enough to provide a compact envelope for transport, shipping, and long-term storage.

By way of summary, the presently preferred embodiments described above incorporate the following features that are useful in maintaining low cost and reduced complexity of the lift-and-rotate mechanism. The moving mass of the mechanism has been greatly reduced, which results in the conservation of actuation energy. Also, since several components of the lift-and-rotate mechanism are stationary, most or all external cable connections can remain stationary during chamber actuation. In addition, the chamber actuation mechanism height and the vent height are such that the vent is higher than the mechanism enclosure. This minimizes the impact of the mechanism and its enclosure on air-flow patterns in and around the vent.

It should be noted that the term "lift-and-rotate mechanism" is being used herein to refer to any suitable assembly that can lift and rotate the chamber. The term "lift-and-rotate mechanism" in the claims should not be limited to the specific designs shown and described in these embodiments and is not intended to be a "means-plus-function" clause under 35 U.S.C. §112, paragraph 6.

It is intended that the foregoing detailed description be understood as an illustration of selected forms that the invention can take and not as a definition of the invention. It is only the following claims, including all equivalents, that are intended to define the scope of this invention.

What is claimed is:

1. A gas flux chamber assembly comprising:
  a base plate;
  a lift-and-rotate mechanism comprising:
    a first generally cylindrical column affixed to the base plate, the first generally cylindrical column including a generally L-shaped slot;
    a second generally cylindrical column positioned within the first generally cylindrical column; the second generally cylindrical column including a helical slot and being rotatable about an axis;
    a third generally cylindrical column positioned within the second generally cylindrical column, the third generally cylindrical column including a hole and being rotatable about the axis and moveable along the axis; and
    a pin passing through the L-shaped slot, the helical slot, and the hole; and a gas flux chamber coupled with the third generally cylindrical column;
wherein the lift-and-rotate mechanism is operative to move the gas flux chamber between first and second positions.

2. The gas flux chamber assembly of claim 1, further comprising a motor coupled with the second generally cylindrical column, wherein the motor is operative to cause the second generally cylindrical column to rotate about the axis.

3. The gas flux chamber assembly of claim 2, wherein the motor comprises a gear motor.

4. The gas flux chamber assembly of claim 2, further comprising a first timing belt pulley coupled with the motor, a second timing belt pulley coupled with the second generally cylindrical column, and a timing belt coupling the first timing belt pulley with the second timing belt pulley.

5. The gas flux chamber assembly of claim 2, wherein actuation of the motor causes the lift-and-rotate mechanism to move the gas flux chamber from the first position to the second position.

6. The gas flux chamber assembly of claim 1, wherein the first position is over a sample and the second position is outside of an area over the sample.

7. The gas flux chamber assembly of claim 1, wherein the gas flux chamber moves approximately 180 degrees between the first position and the second position.

8. The gas flux chamber assembly of claim 1, further comprising a collar coupled with the base plate.

9. The gas flux chamber assembly of claim 8, wherein the gas flux chamber is positioned on the collar in the first position and is positioned outside of an area above the collar in the second position.

10. The gas flux chamber assembly of claim 1, further comprising at least one sensor positioned to detect the position of the gas flux chamber.

11. The gas flux chamber assembly of claim 10, wherein the at least one sensor comprises at least one Hall-effect sensor.

12. The gas flux chamber assembly of claim 10, further comprising a flag coupled with the pin, wherein the at least one sensor is operative to detect movement of the flag.

13. The gas flux chamber assembly of claim 1, further comprising a toothed wheel coupled with the second generally cylindrical column and a sensor positioned to detect movement of the toothed wheel.

14. The gas flux chamber assembly of claim 13, wherein the sensor comprises a Hall-effect sensor.

15. The gas flux chamber assembly of claim 1, further comprising an enclosure, wherein the first generally cylindrical column, the second generally cylindrical column, and at least a portion of the third generally cylindrical column are contained within the enclosure.

16. The gas flux chamber assembly of claim 2, further comprising an enclosure, wherein the first generally cylindrical column, the second generally cylindrical column, at least a portion of the third generally cylindrical column, and the motor are contained within the enclosure.

17. The gas flux chamber assembly of claim 1, further comprising a plurality of feet removably coupled with the base plate.

18. The gas flux chamber assembly of claim 1, wherein a lead angle of the helical slot in the second generally cylindrical column increases near the top of the slot.

19. The gas flux chamber assembly of claim 1, wherein the helical slot comprises two different lead angles, one of which is engaged by the pin during lift, and the other of which is engaged during rotation.

20. The gas flux chamber assembly of claim 1, further comprising:
a spring disk coupled with the gas flux chamber; and
a chamber support structure coupled with the lift-and-rotate mechanism.

21. A method for use with a gas flux chamber assembly, the method comprising:
(a) affixing a first generally cylindrical column to a base plate, the first generally cylindrical column including a generally L-shaped slot;
(b) positioning a second generally cylindrical column, including a helical slot, within the first generally cylindrical column such that the second generally cylindrical column is rotatable about an axis;
(c) positioning a third generally cylindrical column, including a hole, within the second generally cylindrical column such that the third generally cylindrical column is rotatable about the axis and moveable along the axis;
(d) positioning a pin such that it passes through the L-shaped slot, the helical slot, and the hole; and
(e) coupling a gas flux chamber to the third generally cylindrical column;
wherein rotation of the second generally cylindrical column causes the gas flux chamber to be lifted and rotated from a first position to a second position.

22. The method of claim 21, further comprising:
coupling a motor to the second generally cylindrical column, wherein actuation of the motor causes the second generally cylindrical column to rotate and lift and rotate the gas flux chamber from a first position to a second position.

23. The method of claim 21, wherein rotating the second generally cylindrical column causes the gas flux chamber to be lifted and rotated from a first position that is over a sample to a second position that is outside of an area over the sample.

24. The method of claim 21, wherein the second position comprises one of a number of predefined positions.

25. The method of claim 21, wherein the gas flux chamber moves approximately 180 degrees between the first position and the second position.

26. The method of claim 21, further comprising determining the position of the gas flux chamber using at least one sensor.

27. The method of claim 21, further comprising determining the position of the gas flux chamber using at least one sensor and a toothed wheel.

28. The method of claim 21, further comprising placing the first generally cylindrical column, the second generally cylindrical column, and at least a portion of the third generally cylindrical column within an enclosure.

29. The method of claim 22, further comprising placing the first generally cylindrical column, the second generally cylindrical column, at least a portion of the third generally cylindrical column, and the motor within an enclosure.

30. A gas flux chamber assembly comprising:
a base plate;
a lift-and-rotate mechanism comprising:
a motor coupled to the base plate, the motor being fixed with respect to the base plate; and
an arm coupled with the motor, the arm being rotatable about an axis and movable along the axis; and
a gas flux chamber coupled with the arm, the gas flux chamber being movable with respect to the base plate;
wherein the lift-and-rotate mechanism is operative to move the gas flux chamber between first and second positions.

31. The gas flux chamber assembly of claim 30, wherein the motor comprises a gear motor.

32. The gas flux chamber assembly of claim 30, further comprising:
- a first generally cylindrical column affixed to the base plate, the first generally cylindrical column including a generally L-shaped slot;
- a second generally cylindrical column positioned within the first generally cylindrical column; the second generally cylindrical column including a helical slot and being rotatable about an axis;
- a third generally cylindrical column positioned within the second generally cylindrical column, the third generally cylindrical column including a hole and being rotatable about the axis and moveable along the axis; and
- a pin passing through the L-shaped slot, the helical slot, and the hole,
- wherein the arm is coupled with the third generally cylindrical column and the motor is coupled with the second generally cylindrical column.

33. The gas flux chamber assembly of claim 32, further comprising a first timing belt pulley coupled with the motor, a second timing belt pulley coupled with the second generally cylindrical column, and a timing belt coupling the first timing belt pulley with the second timing belt pulley.

34. The gas flux chamber assembly of claim 30, wherein actuation of the motor causes the arm to lift and rotate the gas flux chamber from a first position to a second position.

35. The gas flux chamber assembly of claim 34, wherein the first position is over a sample and the second position is outside of an area over the sample.

36. The gas flux chamber assembly of claim 34, wherein the gas flux chamber moves approximately 180 degrees between the first position and the second position.

37. The gas flux chamber assembly of claim 30, further comprising a collar coupled with the base plate.

38. The gas flux chamber assembly of claim 37, wherein the gas flux chamber is positioned on the collar in a first position and is positioned outside of an area above the collar in a second position.

39. The gas flux chamber assembly of claim 30, further comprising at least one sensor positioned to detect the position of the gas flux chamber.

40. The gas flux chamber assembly of claim 39, wherein the at least one sensor comprises at least one Hall-effect sensor.

41. The gas flux chamber assembly of claim 39, further comprising a flag coupled with the pin, wherein the at least one sensor is operative to detect movement of the flag.

42. The gas flux chamber assembly of claim 30, further comprising a toothed wheel coupled with the gas flux chamber and a sensor positioned to detect movement of the toothed wheel.

43. The gas flux chamber assembly of claim 42, wherein the sensor comprises a Hall-effect sensor.

44. The gas flux chamber assembly of claim 30, further comprising an enclosure, wherein the motor is contained within the enclosure.

45. The gas flux chamber assembly of claim 32, further comprising an-enclosure, wherein the first generally cylindrical column, the second generally cylindrical column, at least a portion of the third generally cylindrical column, and the motor are contained within the enclosure.

46. The gas flux chamber assembly of claim 30, further comprising a plurality of feet removably coupled with the base plate.

47. The gas flux chamber assembly of claim 32, wherein a lead angle of the helical slot in the second generally cylindrical column increases near the top of the slot.

48. The gas flux chamber assembly of claim 32, wherein the helical slot comprises two different lead angles, one of which is engaged by the pin during lift, and the other of which is engaged during rotation.

* * * * *